US011832820B2

(12) United States Patent
Gagner et al.

(10) Patent No.: US 11,832,820 B2
(45) Date of Patent: *Dec. 5, 2023

(54) DEVICES AND METHODS FOR ASSISTING MAGNETIC COMPRESSION ANASTOMOSIS

(71) Applicant: GT METABOLIC SOLUTIONS, INC., Wilmington, DE (US)

(72) Inventors: Michel Gagner, Montréal (CA); Todd A. Krinke, Buffalo, MN (US); Thierry Thaure, San Jose, CA (US)

(73) Assignee: GT METABOLIC SOLUTIONS, INC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/075,984

(22) Filed: Dec. 6, 2022

(65) Prior Publication Data

US 2023/0094285 A1    Mar. 30, 2023

Related U.S. Application Data

(63) Continuation of application No. 17/524,502, filed on Nov. 11, 2021, now Pat. No. 11,534,171.

(Continued)

(51) Int. Cl.
*A61B 17/11* (2006.01)
*A61B 17/00* (2006.01)

(52) U.S. Cl.
CPC . *A61B 17/1114* (2013.01); *A61B 2017/00876* (2013.01)

(58) Field of Classification Search
CPC ........... A61B 2017/00876; A61B 2017/00818; A61B 2017/320073; A61B 17/1114;

(Continued)

(56) References Cited

U.S. PATENT DOCUMENTS 6,332,089 B1 * 12/2001 Acker ...................... A61N 7/02
128/899
6,632,229 B1 * 10/2003 Yamanouchi .......... A61B 17/11
606/159

(Continued)

FOREIGN PATENT DOCUMENTS

EP     1493391 B1    12/2009
EP     2207488 B1     9/2012

(Continued)

OTHER PUBLICATIONS

International Search Report & Written Opinion, International Patent Application No. PCT/US2021/058981, dated Feb. 1, 2022, 18 pages.

*Primary Examiner* — Jocelin C Tanner
(74) *Attorney, Agent, or Firm* — Casimir Jones, SC; Robert A. Goetz

(57) ABSTRACT

A positioning wand for assisting in positioning at least one of a first magnetic implant and a second magnetic implant configured for forming an anastomosis between two adjacent walls of a digestive tract of a patient is provided. The positioning wand can include an elongated member sized and configured to be inserted into an abdominal cavity of the patient, and a distal tip provided at a distal end of the elongated member. The distal tip can include a guide magnet configured to magnetically couple with the at least one of the first and second magnetic implants through a wall of the digestive tract to position the at least one of the first and second magnetic implants to a desired site of the anastomosis. The distal tip can be configured to be moveable in response to a contact pressure upon contact with the wall of the digestive tract.

23 Claims, 14 Drawing Sheets

Related U.S. Application Data

(60) Provisional application No. 63/127,747, filed on Dec. 18, 2020.

(58) Field of Classification Search
CPC .............. A61B 17/7023; A61B 8/4254; A61B 2090/3954; A61B 2090/036; A61B 5/062; A61B 90/03; A61B 90/02; A61F 5/0125; A61M 25/0127; A61M 2205/8287; A61M 60/457

See application file for complete search history.

(56) References Cited

U.S. PATENT DOCUMENTS

| | | |
|---|---|---|
| 7,282,057 B2 | 10/2007 | Surti et al. |
| 7,909,837 B2 | 3/2011 | Crews et al. |
| 8,043,290 B2 | 10/2011 | Harrison et al. |
| 8,262,680 B2 | 9/2012 | Swain et al. |
| 8,506,516 B2 | 8/2013 | Kassab et al. |
| 8,556,919 B2 | 10/2013 | Aguirre et al. |
| 8,623,036 B2 | 1/2014 | Harrison et al. |
| 8,679,139 B2 | 3/2014 | Aguirre et al. |
| 8,728,105 B2 | 5/2014 | Aguirre et al. |
| 8,794,243 B2 | 8/2014 | Deem et al. |
| 8,828,031 B2 | 9/2014 | Fox et al. |
| 8,845,663 B2 | 9/2014 | Chmura |
| 8,915,915 B2 | 12/2014 | Harrison et al. |
| 9,168,041 B2 | 10/2015 | Zaritsky et al. |
| 9,226,753 B2 | 1/2016 | Surti et al. |
| 9,943,335 B2 | 4/2018 | Gittard et al. |
| 10,039,550 B2 | 8/2018 | Altman |
| 10,182,821 B2 | 1/2019 | Lukin et al. |
| 10,285,703 B2 | 5/2019 | Viola |
| 10,342,544 B2 | 7/2019 | Bakos et al. |
| 10,376,400 B2 | 8/2019 | Mcguckin, Jr. |
| 10,448,954 B2 | 10/2019 | Mcweeney et al. |
| 10,555,735 B2 | 2/2020 | Bakos et al. |
| 10,568,630 B2 | 2/2020 | Hernandez et al. |
| 10,624,643 B2 | 4/2020 | Hunt et al. |
| 10,624,644 B2 | 4/2020 | Bakos et al. |
| 10,631,865 B2 | 4/2020 | Bakos et al. |
| 10,682,143 B2 | 6/2020 | Hernandez et al. |
| 10,779,831 B2 | 9/2020 | Lukin et al. |
| 10,813,642 B2 | 10/2020 | Beisel et al. |
| 11,534,171 B2 * | 12/2022 | Gagner ................ A61B 17/1114 |
| 2004/0260273 A1 | 12/2004 | Wan |
| 2008/0114384 A1 | 5/2008 | Chang et al. |
| 2011/0144560 A1 | 6/2011 | Gagner et al. |
| 2012/0078377 A1 | 3/2012 | Gonzales et al. |
| 2012/0179214 A1 | 7/2012 | Geist et al. |
| 2013/0066136 A1 | 3/2013 | Palese et al. |
| 2013/0131440 A1 * | 5/2013 | Gabriel ................... A61F 5/005 606/192 |
| 2016/0287257 A1 | 10/2016 | Fabian et al. |
| 2016/0324523 A1 * | 11/2016 | Lukin ................ A61B 17/1114 |
| 2017/0265866 A1 | 9/2017 | Ryou et al. |
| 2017/0333022 A1 * | 11/2017 | Motai ................ A61B 17/1114 |
| 2018/0028186 A1 | 2/2018 | Yamanouchi |
| 2018/0296218 A1 | 10/2018 | Binmoeller et al. |
| 2019/0133678 A1 | 5/2019 | Pate et al. |
| 2019/0183507 A1 | 6/2019 | Baillargeon |
| 2019/0261998 A1 | 8/2019 | Altman et al. |
| 2019/0274687 A1 | 9/2019 | Wang et al. |
| 2020/0008834 A1 | 1/2020 | Cauche et al. |
| 2020/0129283 A1 | 4/2020 | Swensgard et al. |
| 2020/0138438 A1 * | 5/2020 | Harrison ............ A61B 17/1114 |
| 2020/0323530 A1 | 10/2020 | Sharma |

FOREIGN PATENT DOCUMENTS

| | | |
|---|---|---|
| EP | 2538852 A1 | 1/2013 |
| EP | 3267905 A1 | 1/2018 |
| EP | 2260752 B1 | 3/2018 |
| EP | 3573542 A1 | 12/2019 |
| EP | 3487418 A4 | 4/2020 |
| WO | WO2014055193 A1 | 4/2014 |
| WO | WO2016082481 A1 | 6/2016 |
| WO | WO2019077218 A1 | 4/2019 |
| WO | WO2019232526 A1 | 6/2019 |
| WO | WO2019232527 A1 | 12/2019 |

* cited by examiner

DEVICES AND METHODS FOR ASSISTING MAGNETIC COMPRESSION ANASTOMOSIS

CROSS-REFERENCE TO RELATED APPLICATIONS

The present application is a continuation of U.S. patent application Ser. No. 17/524,502, filed Nov. 11, 2021, which claims priority from U.S. provisional patent application No. 63/127,747, filed on Dec. 18, 2020, and entitled "DEVICES AND METHODS FOR ASSISTING MAGNETIC COMPRESSION ANASTOMOSIS", the disclosures of which are hereby incorporated by reference in their entireties.

TECHNICAL FIELD

The technical field generally relates to medical techniques for treating digestive tract conditions. In particular, the technical field relates to medical techniques including devices for assisting magnetic compression anastomosis in the digestive tract.

BACKGROUND

Metabolic surgeries and medical procedures to treat conditions associated with the digestive tract, diabetes and obesity often require alteration of the digestive tract through incisions, sutures, punctures and/or stapling, which can cause trauma to the organ being altered and lead to bleeding. For instance, bariatric surgery procedures can be used to treat obesity, and can be aimed at bypassing a portion of the stomach and/or the intestine. Such medical procedures can also lead to an increased risk of infection or other complications.

Magnetic compression anastomosis can be used in the context of medical procedures to treat conditions associated with the digestive tract. With magnetic compression anastomosis, necrosis is induced in tissue sandwiched between two magnets. A healing process takes place around the magnets, while the compressed tissue eventually dies and separates from surrounding living tissue. The magnets are released along with the necrotic tissue, leaving an open passage known as an anastomosis.

There remain a number of challenges with respect to surgery procedures performed in the digestive tract, and particularly to the deployment of magnets in the digestive tract.

SUMMARY

In accordance with an aspect, there is provided a positioning wand for assisting in positioning at least one of a first magnetic implant and a second magnetic implant configured for forming an anastomosis between two adjacent walls of a digestive tract of a patient, the positioning wand comprising:
   a handle comprising an elongated member receiving portion;
   an elongated member extending outwardly from the elongated member receiving portion, the elongated member being sized and configured to be inserted into an abdominal cavity of the patient; and
   a distal tip provided at a distal end of the elongated member and being pivotally engaged therewith, the distal tip comprising a guide magnet configured to magnetically couple with the at least one of the first and second magnetic implants through a wall of the digestive tract to position the at least one of the first and second magnetic implants to a desired site of the anastomosis.

In some implementations, the distal tip is pivotally engaged with the elongated member via a pin, the distal tip forming a hinge pivoting back and forth about the pin.

In some implementations, the distal tip has a rectangular cross-section.

In some implementations, the distal tip comprises rounded edges.

In some implementations, the distal tip comprises a wedged distal edge.

In some implementations, the distal tip is pivotally engaged with the elongated member via a pin, the distal tip having a cylindrical shape with a central cylindrical longitudinal axis coinciding with the pin such that the distal tip is rotatable about the central cylindrical longitudinal axis.

In some implementations, the distal tip comprises a frame pivotally engaged with the distal end of the elongated member via a pin, the frame forming a hinge pivoting back and forth about the pin.

In some implementations, the distal tip comprises at least one cylindrical body pivotally engaged with the frame via a cylindrical body pin extending along a central cylindrical body longitudinal axis of a corresponding cylindrical body such that the cylindrical body is rotatable about the central cylindrical longitudinal axis.

In some implementations, at least a portion of the elongated member and associated distal tip are sized and configured to be inserted into the abdominal cavity of the patient laparoscopically.

In some implementations, the at least a portion of the elongated member is sized and configured to be inserted into the abdominal cavity of the patient through a trocar.

In some implementations, the trocar has an internal diameter ranging from about 3 mm and 15 mm.

In some implementations, the elongated member has an external diameter ranging from about 2 mm and about 14 mm.

In some implementations, the elongated member is rigid.

In some implementations, the elongated member is flexible.

In some implementations, the elongated member includes at least one flexible portion and at least one rigid portion.

In some implementations, the at least one flexible portion is closer to the distal tip than the at least one rigid portion.

In some implementations, the elongated member is sized and configured to be inserted into the abdominal cavity of the patient via a NOTES procedure.

In some implementations, the elongated member comprises a tubular structure.

In some implementations, the tubular structure defines a channel extending along a longitudinal axis of the elongated member.

In some implementations, the channel is configured to receive a guide wire therein, the guide wire being connected to the distal tip to form a flexible connection between the distal end of the elongate member and the distal tip.

In some implementations, the distal tip is configurable between a distal tip retracted configuration and a distal tip deployed configuration.

In some implementations, the guide wire is further configured to steer the elongated member.

In some implementations, the distal tip is releasable from the distal end of the elongated member.

In some implementations, the tubular structure comprises a plurality of tubular structures.

In some implementations, the plurality of tubular structures is provided in a telescopic configuration.

In some implementations, the elongated member is configurable in an elongated member retracted configuration and an elongated member deployed configuration.

In some implementations, the tubular structures of the plurality of tubular structures are flexibly connected to each other.

In some implementations, the distal tip comprises a housing configured to house the guide magnet therein.

In some implementations, the housing of the distal tip fully encloses the guide magnet therein.

In some implementations, the guide magnet of the distal tip comprises multiple magnets.

In some implementations, the multiple magnets are provided in a spaced-apart relationship relative to each other.

In some implementations, the multiple magnets are hingedly connected to each other via respective hinge connections.

In some implementations, the housing is rigid.

In some implementations, the housing is flexible.

In some implementations, the housing is made of a biocompatible polymeric material.

In some implementations, the housing is made of a metallic material.

In some implementations, the housing comprises a smooth outer surface that is configured to contact the wall of the digestive tract.

In some implementations, the smooth outer surface is lubricious.

In some implementations, the housing comprises a connecting member connectable to a connector extending from the elongated member.

In some implementations, the connecting member is releasably connectable to the connector.

In some implementations, the connector comprises a snare.

In some implementations, the connecting member comprises a pommel snare or a knob.

In some implementations, the connector comprises a grabber comprising a U-shaped jaw.

In some implementations, the U-shaped jaw is mechanically actuated.

In some implementations, the connecting member comprises a loop receivable in the U-shaped jaw.

In some implementations, the loop comprises a biocompatible braided wire, a polymer wire, or a nitinol wire.

In some implementations, the connector comprises a grabber comprising a slot feature.

In some implementations, the connecting member comprises a ball receivable in the slot feature.

In some implementations, the guide magnet of the distal tip comprises an electromagnet.

In some implementations, the guide magnet of the distal tip comprises a non-permanent magnet.

In some implementations, the distal tip comprises a sensor for detecting a magnetic field.

In some implementations, the handle comprises includes a finger receiving portion and a thumb receiving portion.

In some implementations, the positioning wand further comprises one or more features as defined herein and/or described herein and/or illustrated herein.

In accordance with another aspect, there is provided a method for positioning at least one of first and second magnetic implants configured for forming an anastomosis at a target site between two adjacent walls of a digestive tract of a patient, the method comprising:

deploying the first magnetic implant into a first hollow organ lumen defining a first region of the digestive tract;

deploying the second magnetic implant into a second hollow organ lumen defining a second region of the digestive tract;

inserting a distal tip and at least a portion of an elongated member of a positioning wand into an abdominal cavity of the patient, the distal tip being movably engaged with a distal end of the elongated member and comprising a guide magnet;

magnetically coupling the distal tip of the positioning wand with the second magnetic implant; and displacing the distal tip of the positioning wand within the abdominal cavity while maintaining the magnetic coupling with the second magnetic implant to bring the second magnetic implant in close proximity with the first magnetic implant to magnetically couple the first magnetic implant with the second magnetic implant.

In some implementations, bringing the second magnetic implant in close proximity with the first magnetic implant comprises bringing the second region of the digestive tract in close proximity to the first region of the digestive tract to magnetically couple the first magnetic implant with the second magnetic implant.

In some implementations, displacing the distal tip of the positioning wand within the abdominal cavity while maintaining the magnetic coupling with the second magnetic implant comprises conforming a wall-contacting surface of the distal tip against an outer surface of a wall of a second hollow organ having the second hollow organ lumen.

In some implementations, displacing the distal tip of the positioning wand within the abdominal cavity while maintaining the magnetic coupling with the second magnetic implant comprises translating the wall-contacting surface of the distal tip against the outer surface of the wall of the second hollow organ having the second hollow organ lumen.

In some implementations, conforming the wall-contacting surface of the distal tip against the outer surface of the wall of the second hollow organ having the second hollow organ lumen comprises hingedly moving the distal tip relative to the distal end of the elongated member.

In some implementations, conforming the wall-contacting surface of the distal tip against the outer surface of the wall of the second hollow organ having the second hollow organ lumen comprises establishing a flexible connection between the distal tip relative to the distal end of the elongated member.

In some implementations, displacing the distal tip of the positioning wand within the abdominal cavity while maintaining the magnetic coupling with the second magnetic implant comprises rotating the wall-contacting surface of the distal tip against the outer surface of the wall of the second hollow organ having the second hollow organ lumen.

In some implementations, the method further comprises maintaining at least one of the first and second hollow organs in a given position via a non-magnetic laparoscopic instrument while displacing the distal tip of the positioning wand within the abdominal cavity.

In some implementations, inserting the distal tip and the at least a portion of the elongated member into the abdominal cavity of the patient comprises inserting the distal tip and the at least a portion of an elongated member laparoscopically.

In some implementations, inserting the distal tip and the at least a portion of the elongated member laparoscopically comprises inserting the distal tip and the at least a portion of the elongated member through a trocar.

In some implementations, inserting the distal tip and the at least a portion of the elongated member into the abdominal cavity of the patient comprises inserting the distal tip and the at least a portion of the elongated member into a natural orifice of the patient.

In some implementations, the method further comprises inserting the distal tip and the at least a portion of an elongated member transluminally.

In some implementations, the method further comprises magnetically uncoupling the distal tip and the second magnetic implant to retrieve the distal tip and the at least a portion of the elongated member from the abdominal cavity of the patient.

In some implementations, the method further comprises navigating the distal tip into the abdominal cavity to detect a magnetic field indicative of a location of the first magnetic implant or the second magnetic implant.

In some implementations, the method further comprises placing a marker at an intended location of the first or second magnetic implant to mark the target site of the anastomosis, and navigating the distal tip of the positioning wand based on a placement of the marker.

In some implementations, the marker comprises a magnetic clip.

In some implementations, navigating the distal tip of the positioning wand based on the placement of the marker comprises magnetically coupling the magnetic clip and the distal tip.

In some implementations, the marker comprises a non-magnetic clip.

In some implementations, navigating the distal tip of the positioning wand based on the placement of the marker comprises mechanically coupling the non-magnetic clip and the distal tip.

In some implementations, the method further comprises releasing the distal tip from the distal end of the elongated member.

In some implementations, releasing the distal tip from the distal end of the elongated member comprises maintaining a flexible connection between the distal tip and a guide wire extending within the elongated member.

In some implementations, following the magnetic coupling between the distal tip and the second magnetic implant, the elongated member is movable to another region within the abdominal cavity.

In some implementations, bringing the second magnetic implant in close proximity with the first magnetic implant comprises retracting the distal tip to the distal end of the elongated member to bring the second region of the digestive tract in close proximity to the first region of the digestive tract to magnetically couple the first magnetic implant with the second magnetic implant.

In some implementations, releasing the distal tip from the distal end of the elongated member comprises terminating a connection between the distal tip and a guide wire extending within the elongated member.

In some implementations, releasing the distal tip from the distal end of the elongated member comprises releasing both the distal tip and a guide wire extending within the elongated member from the elongated member.

In some implementations, following the magnetic coupling between the distal tip and the second magnetic implant, the elongated member is movable to another region within the abdominal cavity.

In some implementations, bringing the second magnetic implant in close proximity with the first magnetic implant comprises using an additional instrument to bring the second region of the digestive tract in close proximity to the first region of the digestive tract to magnetically couple the first magnetic implant with the second magnetic implant.

In some implementations, the method further comprises one or more features as defined herein and/or described herein and/or illustrated herein.

In accordance with another aspect, there is provided a positioning wand for assisting in positioning at least one of a first magnetic implant and a second magnetic implant configured for forming an anastomosis between two adjacent walls of a digestive tract of a patient, the positioning wand comprising:
  an elongated member sized and configured to have at least a portion thereof to be inserted into an abdominal cavity of the patient; and
  a distal tip provided at a distal end of the elongated member and comprising a guide magnet configured to magnetically couple with the at least one of the first and second magnetic implants through a wall of the digestive tract to position the at least one of the first and second magnetic implants to a desired site of the anastomosis, the distal tip being configured to be moveable in response to a contact pressure upon contact with the wall of the digestive tract.

In some implementations, the distal tip is pivotally engaged with the elongated member via a pin, the distal tip forming a hinge pivoting back and forth about the pin.

In some implementations, the distal tip has a substantially rectangular cross-section.

In some implementations, the distal tip comprises a wedged distal edge.

In some implementations, the distal tip comprises rounded edges.

In some implementations, the distal tip is pivotally engaged with the elongated member via a pin, the distal tip having a cylindrical shape with a central cylindrical longitudinal axis coinciding with the pin such that the distal tip is rotatable about the central cylindrical longitudinal axis.

In some implementations, the distal tip comprises a frame pivotally engaged with the distal end of the elongated member via a pin, the frame forming a hinge pivoting back and forth about the pin.

In some implementations, the distal tip comprises at least one cylindrical body pivotally engaged with the frame via a cylindrical body pin extending along a central cylindrical body longitudinal axis of a corresponding cylindrical body such that the cylindrical body is rotatable about the central cylindrical longitudinal axis.

In some implementations, the distal tip is engaged with the elongated member via a spherical swiveling joint.

In some implementations, the distal tip is engaged with the distal end of the elongated member via a biasable connection.

In some implementations, the biasable connection comprises a spring.

In some implementations, the biasable connection comprises a biasable neck extending between the distal end of the elongated member and the distal tip.

In some implementations, the distal tip is configured to be moveable in response to the contact pressure upon contact with the wall of the digestive tract to lighten the contact pressure.

In some implementations, the positioning wand further comprises one or more features as defined herein and/or described herein and/or illustrated herein.

In accordance with another aspect, there is provided a system for forming an anastomosis between two adjacent walls of a digestive tract, the system comprising:

first and second elongated magnetic implants configured to magnetically couple to each other through the two adjacent walls of the digestive tract to compress a portion of the two adjacent walls therebetween and form a necrotic area that becomes surrounded by a scarred edge following a healing time period; and a positioning wand comprising:
an elongated member sized and configured to have at least a portion thereof to be inserted into an abdominal cavity of the patient; and
a distal tip provided at a distal end of the elongated member and comprising a guide magnet configured to magnetically couple with the first magnetic implant through a wall of the digestive tract to position the first magnetic implant to a desired site of the anastomosis, the distal tip being configured to be moveable in response to a contact pressure upon contact with the wall of the digestive tract.

In some implementations, the distal tip is pivotally engaged with the elongated member via a pin, the distal tip forming a hinge pivoting back and forth about the pin.

In some implementations, the distal tip is pivotally engaged with the elongated member via a pin, the distal tip having a cylindrical shape with a central cylindrical longitudinal axis coinciding with the pin such that the distal tip is rotatable about the central cylindrical longitudinal axis.

In some implementations, the distal tip comprises a frame pivotally engaged with the distal end of the elongated member via a pin, the frame forming a hinge pivoting back and forth about the pin.

In some implementations, the distal tip comprises at least one cylindrical body pivotally engaged with the frame via a cylindrical body pin extending along a central cylindrical body longitudinal axis of a corresponding cylindrical body such that the cylindrical body is rotatable about the central cylindrical longitudinal axis.

In some implementations, the distal tip is engaged with the elongated member via a spherical swiveling joint.

In some implementations, the distal tip is engaged with the distal end of the elongated member via a biasable connection.

In some implementations, at least one of the first and second elongated magnetic implants comprises a flat compression surface.

In some implementations, the elongated member includes at least one flexible portion and at least one rigid portion.

In some implementations, the elongated member comprises a tubular structure defining a channel extending along a longitudinal axis of the elongated member, the channel being configured to receive a guide wire therein, the guide wire being connected to the distal tip to form a flexible connection between the distal end of the elongated member and the distal tip.

In some implementations, the elongated member comprises a plurality of tubular structures provided in a telescopic configuration.

In some implementations, the distal tip comprises multiple segments hingedly connected to each other via respective hinge connections.

In some implementations, the multiple segments form a flexible train conformable to an outer surface of the wall of the digestive tract.

In some implementations, the distal tip comprises multiple segments connected in series via a flexible wire.

In some implementations, the guide magnet of the distal tip comprises a plurality of guide magnets received in a single flexible housing.

In some implementations, guide magnet of the distal tip comprises a plurality of guide magnets each received in a corresponding housing.

In some implementations, the system further comprises one or more features as defined herein and/or described herein and/or illustrated herein.

BRIEF DESCRIPTION OF THE DRAWINGS

The attached figures illustrate various features, aspects and implementations of the technology described herein.

DETAILED DESCRIPTION

Techniques described herein relate to systems, devices and methods for assisting in the deployment and coupling of magnetic implants used for forming a magnetic compression anastomosis between two adjacent walls of hollow structures of the digestive tract of a patient, in the context of procedures to treat various medical conditions associated with the digestive tract. Such assistance can include visualization of anatomical targets and of magnetic implants, movement of anatomical structures, and alignment of magnetic implants to enable their magnetic coupling.

The formation of the anastomosis can be achieved without puncturing the tissue of the hollow structures through which the anastomosis is formed, for example by inserting a first magnetic implant into the lumen of a first hollow organ and a second magnetic implant into the lumen of a second hollow organ, positioning the first and second magnetic implants at a desired anastomosis site, and by magnetically coupling the first and second magnetic implants together to compress the tissue of the adjacent walls therebetween. Compression of the wall tissue between the two magnetic implants results in a necrotic area that corresponds approximately to the surface area of the compression surface of the magnetic implant pair. Over time, the necrotic area becomes surrounded by an edge of scar tissue, which can also be referred to as a scarred edge.

The positioning of at least one of the magnetic implants at the desired site of the anastomosis can be performed via the assistance of a positioning wand interacting with the magnetic implant within the abdominal cavity of the patient. The positioning wand can be manipulated by a healthcare provider, such as a physician, and a portion of the positioning wand can be introduced into the abdominal cavity of a patient using a minimally invasive surgery. Minimally invasive surgeries can include laparoscopic surgeries, which typically includes cooperation of a laparoscopic instrument with a trocar to facilitate introduction of the laparoscopic instrument into the abdominal cavity, percutaneous laparoscopy, which can enable introduction into the abdominal cavity without the use of a trocar, and Natural Orifice Transluminal Endoscopic Surgery (NOTES) procedures, for example.

Various implementations and features of the positioning wand and associated methods will now be described in greater detail in the following paragraphs.

General Description of a System for Forming a Magnetic Compression Anastomosis

A general description of a system for forming a magnetic compression anastomosis between two adjacent wall of the digestive tract of a patient will now be provided, and the description of a positioning wand for assisting in the positioning at least one of the magnetic implant at the desired site of the anastomosis will follow thereafter.

Figure 1:
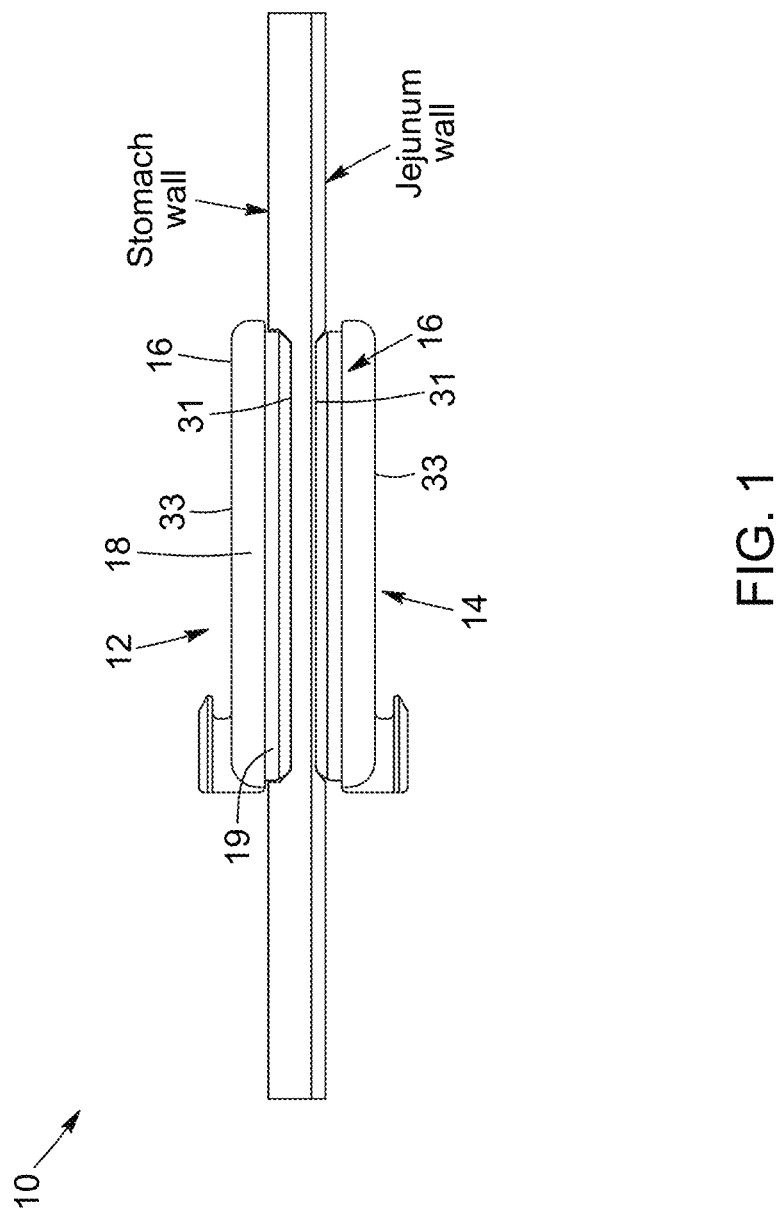
FIG. 1 is a side view of first and second magnetic implants, with the first magnetic implant being shown in contact with a vessel wall of a first hollow organ and the second magnetic implant being shown in contact with a vessel wall of a second hollow organ, at the desired site of the anastomosis.

With reference to FIG. 1, a system 10 for forming an anastomosis between two adjacent walls of hollow organs of the digestive tract is shown. In the implementation shown, the system 10 includes a first magnetic implant 12 for implantation in the stomach, and a second magnetic implant 14 for implantation in the jejunum. It is to be understood that the term "implant" refers to a device that is implanted in the digestive tract for a certain period of time sufficient to enable formation of the anastomosis. As used herein, the term "implant" can be used interchangeably with the term "device" or "component", for instance. In the implementation shown, the stomach represents a first hollow organ of the digestive tract into which the first magnetic implant 12 can be implanted, and the jejunum represents a second hollow organ into which the second magnetic implant 14 can be implanted, so as to compress a portion of the stomach wall and a portion of the jejunum wall therebetween.

In the implementation shown, the magnetic implant includes a housing 16 configured to enclose a magnet therein to form the corresponding magnetic implant. The housing 16 includes an outward portion 18 and an inward portion 19. The inward portion 19 of the housing 16 faces the corresponding other magnetic implant once the magnetic implants 12, 14 are magnetically coupled, and is involved in the magnetic compression of the tissue, while the outward portion 18 of the housing 16 is on the opposed side of the magnetic implant and facing away from the tissue being compressed. In the illustrated implementation, the housing 16 surrounds the magnet. Other housing constructions are also possible, where one or more housing components are used to partly or fully enclose the magnet.

Still referring to FIG. 1, the first magnetic implant 12 is a device that is implantable into a first hollow organ of the digestive tract of a patient at a site of a desired anastomosis via the lumen of the first hollow organ. Examples of hollow organs of the digestive tract include the oesophagus, stomach, duodenum, jejunum, ileum, colon, biliary tract, and pancreatic duct. A site of desired anastomosis can be determined according to the condition of the patient, and this aspect will not be discussed further in the context of the present description. As used herein, the expression "magnetic implant" refers to a structure that can be implanted into the chosen hollow organ of the digestive tract, and that can be magnetically attracted to another magnetic implant due to magnetic forces. In some implementations, the magnetic implant can consist of a magnet. In some implementations, the magnetic implant can include a magnet and one or more additional features, such as a housing and/or a connecting member. The two magnetic implants can be substantially the same as each other, or different, in terms of their shape, configuration, construction, and/or material make-up.

The first magnetic implant 12 is used with a second magnetic implant 14 to form an implant pair. The second magnetic implant 14 is a device implantable into a second hollow organ of the digestive tract of the patient to the site of the desired anastomosis via the lumen of the second hollow organ. The second hollow organ of the digestive tract can be located in sufficiently close proximity of the first hollow organ to enable the convergence of the respective wall tissue of the first hollow organ and the second hollow organ to eventually form the anastomosis, which can be achieved using the positioning wand as described herein.

Each one of the first and second magnetic implants 12, 14 can have any suitable shape and size determined in accordance with their intended purpose. In some implementations, the size and the shape of the magnetic implant can be determined for instance in accordance with the characteristics of the site of the desired anastomosis, the delivery technique chosen to deliver the magnetic implant to the site of the desired anastomosis, and so on. In some implementations, the magnetic implant can have for example an elliptic shape, a circular shape, an elongated shape, a rectangular shape, an octagonal shape, or any other polygonal shape in terms of its cross-section. The magnetic implant can include rounded corners to facilitate navigation into the digestive tract. The magnetic implant can have an aspect ratio of about 1:1 (e.g., in the case of a circular cross-section) or an aspect ratio of about 1:2 to 1:40, about 1:3 to 1:20, about 1:4 to 1:15, for example, or another aspect ratio. In some implementations, the height of the magnetic implant can be proportional to the thickness of the magnet contained therein and hence desired magnetic strength.

Each of the first and second magnetic implants 12, 14 includes a compression surface 30 that is configured to contact the tissue of the corresponding hollow organ. The compression surface 31 can also be referred to as a tissue-contacting surface, since it is the compression surface 31 of the magnetic implant that is eventually in contact with the interior wall of the hollow organ once the magnetic implant is delivered to the site of the desired anastomosis. In some implementations, the compression surface 31 can be a flat compression surface. The compression surface 31 can be substantially continuous. In other implementations, the compression surface 31 of the first magnetic implant 12 can have a complementary shape compared to the compression surface 31 of the second magnetic implant 14. In other implementations, the compression surface 31 can include features such as ridges, crests, furrows, grooves, and the like. For instance, the compression surface 31 of the first magnetic implant 12 can include a series of ridges, and the second magnetic implant 14 can include a complimentary series of furrows such that when the first and second magnetic implants 12, 14 are magnetically coupled, the first and second magnetic implants 12, 14 can interlock and/or self-align to increase the stability of their positioning on their respective sides of the first and second hollow organs. Each of the first and second magnetic implants 12, 14 also includes a lumen-oriented surface 33 opposite the tissue-contacting surface, the lumen-oriented surface 33 generally facing the lumen of the hollow organ once the magnetic implant is delivered to the site of the desired anastomosis.

Each one of the first and second magnetic implants 12, 14 can be navigated to the site of the desired anastomosis using various techniques. For instance, the magnetic implants 12, 14 can be delivered to the site of the desired anastomosis endoscopically. A positioning wand as described herein can then be used to facilitate the positioning of at least one of the first and second magnetic implants 12, 14 to the desired site of the anastomosis. For instance, in some implementations, the positioning wand can facilitate convergence of the respective wall tissue of the first hollow organ and the second hollow organ, such that the magnetic implants 12, 14 can be brought in sufficiently close proximity to enable their magnetic coupling.

In some implementations, the magnetic implants 12, 14 can have smooth outer surfaces and rounded edges to minimize sliding resistance and tissue trauma along the inner walls of the gastrointestinal tract. In some implementations, the smooth outer surfaces of the magnetic implants 12, 14 can be provided by a lubricious coating, a hydrophilic coating or a polymeric coating, for instance. The magnetic implants 12, 14 can be axially symmetrical, so that the health care provider can move and align the magnetic implant proximally or distally. The magnetic implant can also incorporate fluorescent or radiopaque dye or markers to aid optical or fluoroscopic visualization.

The positioning wand will now be described in further detail.

Figure 2:
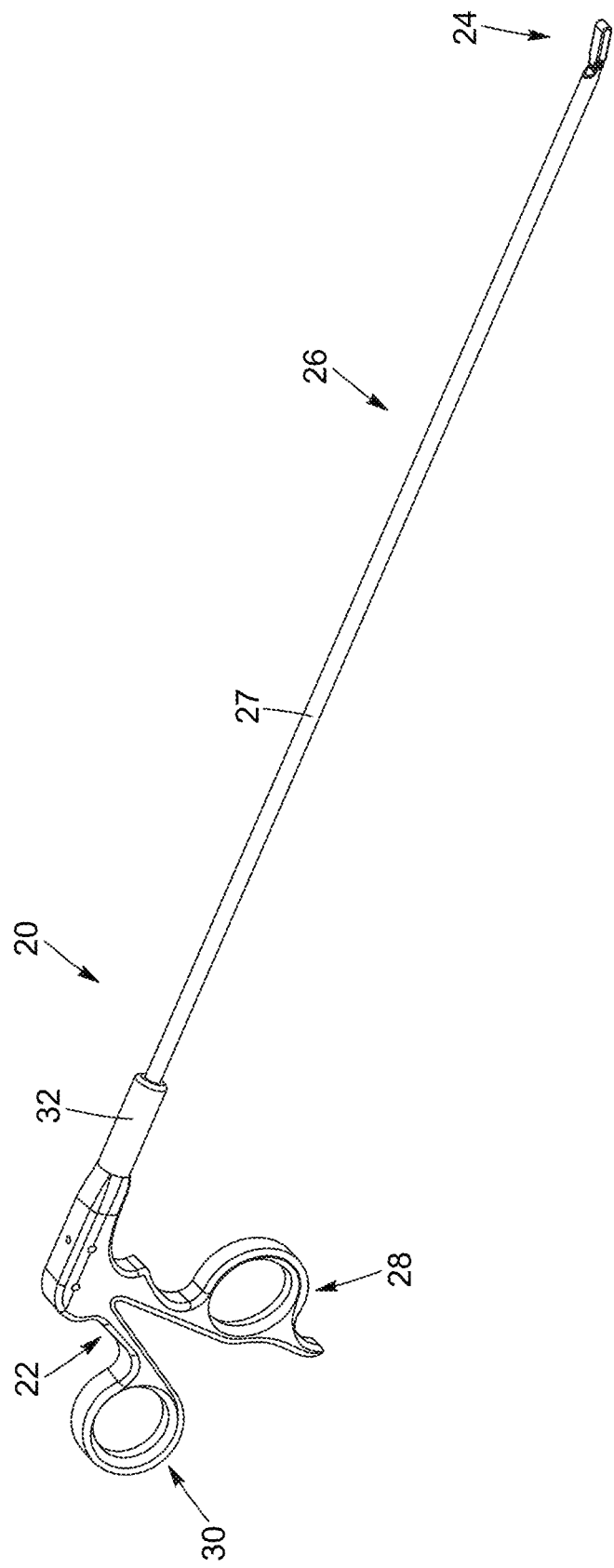
FIG. 2 is a perspective view of a positioning wand that includes a distal tip and a handle.

Description of a Positioning Wand for Assisting in the Deployment and Positioning of a Magnetic Implant or a Pair of Magnetic Implants Referring now to FIG. 2, an implementation of a positioning wand 20 is shown. The positioning wand 20 includes a handle 22 at a proximal end thereof, a distal tip 24 at a distal end thereof, and an elongated member 26 extending between the handle 22 and the distal tip 24. The combination of the handle 22, elongated member 26 and distal tip 24 enables interaction with the magnetic implant within the abdominal cavity of the patient. It is to be noted that in the context of the present description, the expression "positioning wand" can be used interchangeably with the expression "positioning device".

Elongated Member

The elongated member 26 can have various configurations. In some implementations, the elongated member 26 can include one or more tubular structures provided in a longitudinally adjacent relationship to provide a desired length of the elongated member 26. The tubular structure can be rigid or flexible. Accordingly, the elongated member 26 can include a single tubular structure that is rigid or flexible, or the elongated member 26 can include a plurality of tubular structures that are flexible or rigid, or can include a combination of tubular structures that are flexible and of tubular structures that are rigid. In some implementations, when the elongated member 26 includes a plurality of tubular structures, the tubular structures can be rigid, and the connection between adjacent tubular structures can be such that the resulting entire length of the elongated member 26 is rigid. Alternatively, when the elongated member 26 includes a plurality of tubular structures, the connection between two adjacent tubular structures can be such that one of the tubular structure can move relative to the adjacent tubular structure, thereby conferring flexibility to at least a portion of the elongated member 26. For instance, enabling movement of a distal one of the tubular structures relative to a proximal one of the tubular structures can facilitate navigating the elongated member 26 to a desired location within the abdominal cavity of the patient. When the connection between two adjacent tubular structures is flexible, the flexibility of the connection can be provided for instance by a material that is more flexible than the material from which is made the tubular structure. For example, the flexible connection can be made of a polymer such as silicone. In some implementations, when the elongated member 26 includes a plurality of tubular structures, the plurality of tubular structures can be provided in a telescopic relationship to form a telescopic assembly of tubular structures. The telescopic assembly of tubular structures can enable adjusting the length of the elongated member 26 so that the elongated member 26 can be switched from a deployed configuration when a given length of the elongated member 26 is desired, for instance to reach a certain location within the abdominal cavity, to a retracted configuration when a shorter length of the elongated member 26 is desired or for storage of the positioning wand 20.

The tubular structure forming the elongated member 26 can be hollow and define a channel extending along a longitudinal axis thereof. When a plurality of tubular structures is provided, the hollow configuration of the tubular structure can enable the elongated member 26 to adopt the telescopic configuration described above. The hollow configuration of the tubular structure can enable the passage of one or more pull wires, or guide wires, therein. In such implementations, the hollow tubular structure thus serves as a housing for receiving the one or more pull wires. The presence of a pull wire within the channel of the tubular structure can contribute to facilitating steering of the elongated member 26, when the elongated member 26 is made of at least one tubular structure that is flexible or that includes a plurality of the tubular structures that are flexibly connected with each other. Once again, being able to steer the elongated member 26 via the action of the pull wire can be beneficial to deploy the positioning wand 20 to a desired location within the abdominal cavity of the patient.

In the implementation shown in FIG. 2, the elongated member 26 includes a single tubular structure 27 that is substantially rigid.

The dimensions of the elongated member 26 can vary depending on the intended application or maneuver for which the positioning wand 20 is to be used for. In some implementations, the elongated member 26 can be configured to fit through a laparoscopic trocar having an internal diameter ranging from about 3 mm to about 15 mm. Accordingly, in such implementations, the external diameter of the elongated member 26 can range for instance from about 2 mm to about 14 mm.

The elongated member 26 can also be configured to enter the abdominal cavity through a NOTES procedure. In such implementations, the elongated member 26 is generally flexible to facilitate navigation thereof through the sinuous pathway of the digestive tract. A NOTES procedure is a procedure that involves gaining access to the abdominal cavity by entering the digestive tract through a natural orifice rather than percutaneously. The natural orifice can vary depending on the location that is to be reached, and can include the mouth, the anus, or the vagina. Access via the mouth can enable a distal portion of the elongated member 26 to enter the stomach with the option of travelling further down in the digestive tract towards the small intestine, similarly to how an endoscope would be used, while access via the anus can enable a distal portion of the elongated member 26 to enter the colon and travel up towards the small intestine, similarly to how a colonoscope would be used. The wall of the digestive tract can then be breached to enable passage of the elongated member 26 therethrough such that the elongated member 26 can enter the abdominal cavity at a chosen location. When the NOTES procedure is performed via the mouth and the incision is made through the wall of the stomach, the procedure can be referred to as a transgrastic NOTES procedure. The incision made through the wall of the digestive tract can then be sutured using endoscopically administered clips, for instance. A NOTES procedure can thus avoid an incision of the abdominal wall of the patient, which can also avoid complications that can occur from abdominal wall incisions, such as hernias or wound infections. In some implementations, the use of an elongated member 26 that is flexible can facilitate access to remote areas of the peritoneal cavity more easily and quickly compared to a rigid elongated member 26.

Thus, it will be understood that the characteristics of the elongated member 26, for instance in terms of dimensions and properties, can be determined and adapted in accordance with the intended use of the positioning wand 20 and more particularly, on the location of the desired site of the magnetic compression anastomosis and the maneuvers that have to be performed in the abdominal cavity to access the desired site of the magnetic compression anastomosis.

Handle

The handle 22 of the positioning wand 20 can be any type of structure that enables manual manipulation of the positioning wand 20 by the health care provider. In some implementations, the handle 22 can include a control mechanism that enables control of a pull wire received in the channel of the tubular structure of the elongated member 26 such that the elongated member 26 can be steered as desired. The handle 22 of the positioning wand 20 can also include a control mechanism that enables modifying a configuration of the distal tip 24. For instance, the control mechanism can enable changing the configuration of the distal tip 24 from a grasping configuration to a releasing configuration. When in the grasping configuration, the distal tip 24 can be used to grasp a portion of tissue of a given organ of the abdominal cavity to displace the given organ, or to grasp a given instrument to carry it to a given location. When in the releasing configuration, the distal tip 24 then releases the given organ or given instrument that it was previously grasping. In some implementations, the control mechanism of the handle 22 can also be configured to enable release of the distal tip 24, when the distal tip 24 is provided as a releasable distal tip.

The handle 22 can include portions configured to facilitate manipulation of the handle 22 and associated features of the positioning wand 20 by the health care provider. In the implementations shown in FIG. 2, the handle 22 includes a finger receiving portion 28 and a thumb receiving portion 30. The finger receiving portion 28 and the thumb receiving portion 30 can enable the health care provider to manipulate the handle 22 in a scissor-like fashion, for instance to guide the pull wire that may be received in the channel of the tubular structure of the elongated member 26, which in turn can contribute to modify the position of the distal tip 24. The handle 22 also includes an elongated member receiving portion 32 configured to engage with the elongated member 26 such that the elongated member 26 extends distally therefrom.

In some implementations, the handle 22 can be operatively connected to the distal tip 24 via an electric circuit or an electromagnet circuit. Additional details regarding this aspect are provided below.

Distal Tip

Details regarding the engagement of the distal tip 24 with the elongated member 26 and the configuration of the distal tip 24 will now be provided.

The distal tip 24 of the positioning wand 20 is configured to magnetically interact with at least one of the magnetic implants 12, 14, to aid in the placement of the magnetic implants 12, 14 at the desired site of the anastomosis. Once a magnetic interaction of the distal tip 24 with a magnetic implant has been established, the health care provider can move the distal tip 24 to bring the magnetic implant at the desired site of the anastomosis. Moving the magnetic implant via a magnetic interaction with the distal tip 24 can involve for instance sliding the distal tip 24 along the wall of an organ of the digestive tract, such as the small intestine, or rotating or rolling the distal tip 24 along the wall of an organ of the digestive tract. The distal tip 24 can also be configured to be moveable in response to a contact pressure upon contact with the wall of the digestive tract to lighten the contact pressure, to minimize tissue trauma to the wall of the organ of the digestive tract.

With reference to FIGS. 3 to 8, the distal tip 24 of the positioning wand 20 can have various shapes and configurations. For instance, the distal tip 24 can have an elongated shape, a rectangular shape, a cylindrical shape, an oblong or stadium shape, an elliptic shape, a "pill" shape, or a wedged shaped. The distal tip 24 can include atraumatic edges to facilitate insertion and navigation into the digestive tract and the abdominal cavity. When referring to a rectangular shape, it is to be understood that the cross-section of the distal tip 24 can be rectangular, and the distal tip 24 can have the shape of a rectangular prism.

In some implementations, the distal tip 24 can have a length ranging from about 3 mm to about 60 mm, and a width ranging from about 2 mm to about 14 mm. In some implementations, the distal tip 24 can have a length of up to 100 mm. When a laparoscopic trocar is used to introduce the positioning wand 20 into the abdominal cavity of the patient, the width of the distal tip 24 can be determined so as to fit within to opening formed by the laparoscopic trocar. The combination of the length and width of the distal tip 24 can be determined to achieve a given surface area of the distal tip 24 to efficiently interact with the magnetic implant, and accordingly to achieve a given magnetic load of the distal tip 24. For instance, it may be desired to achieve a given surface area of the distal tip 24 that enables distributing the magnetic load over such given surface area to minimizing tissue trauma to the wall of the organ of the digestive tract. In some scenarios, a larger surface area of the distal tip 24 can contribute to minimizing tissue trauma to the wall of the organ of the digestive tract.

Figure 4:
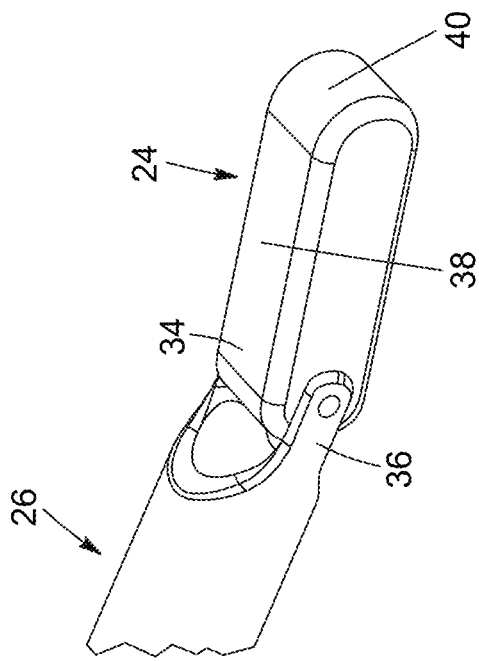
FIG. 4 is an enlarged view of a portion of a positioning wand showing another example of a distal tip of the positioning wand.
Figure 3:
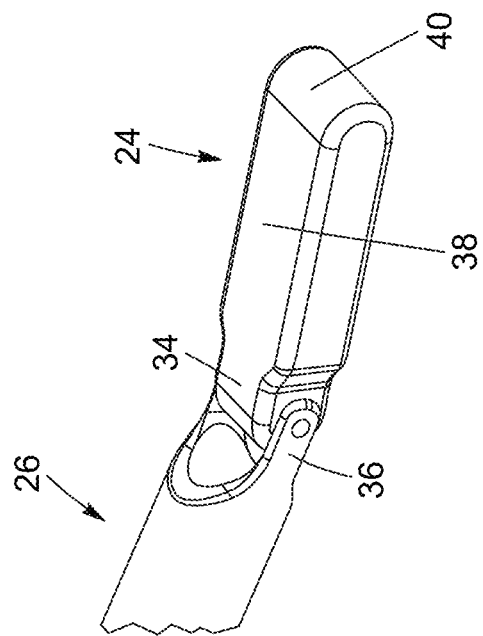
FIG. 3 is an enlarged view of a portion of a positioning wand showing an example of a distal tip of the positioning wand.

FIGS. 3 and 4 illustrate an implementation where the distal tip 24 has an oblong shape that is elongated along a longitudinal axis of the elongated member 26, and that includes rounded corners and edges to facilitate navigation into the digestive tract and/or the abdominal cavity. In the illustrated implementations shown in FIGS. 3 and 4, a proximal portion 34 of the distal tip 24 is pivotally engaged with the distal end 36 of the elongated member 26, and the remainder of the body 38 of the distal tip 24, including the distal portion 40 of the distal tip 24, extends longitudinally from the distal end 36 of the elongated member 26. The pivotable engagement can be achieved via a pin coupled to a hinge. Multiple pin and hinge couplings can be provided in parallel, to provide multiple in-line pivotable engagements. In some implementations, multiple pins may be oriented orthogonally, to create one or more universal joints as the pivotable engagement. The pivotal engagement enables the distal tip to pivot back and forth about the pin.

The pivotable engagement of the proximal end 34 of the distal tip 24 with the distal end 36 of the elongated member 26 can enable the distal tip 24 to rotate around a rotation axis that is perpendicular to the longitudinal axis of the elongated member 26. For instance, in FIGS. 3 and 4, the distal tip 24 could be considered as being configured to move up and down in relation to the distal end 36 of the elongated member 26, although the distal tip 24 could also be considered as being configured to move side to side in relation to the distal end 36 of the elongated member 26 following a rotation of 90° of the elongated member 26. Thus, the distal tip 24 of the positioning member 20 can move in several directions when the elongated member 26 is manipulated to be rotated around its longitudinal axis.

FIG. 3 illustrates a distal tip 24 having a proximal portion 34 that has a reduced width compared to the remainder of the body 38 of the distal tip 24. In some implementations, the reduced width of the proximal portion 34 of the distal tip 24 can facilitate the cooperation with the distal end 36 of the elongated member 26. The variation of the width of the distal tip 24 along a length thereof can also enable adapting the width of the proximal portion 34 of the distal tip 24 to the diameter, or width, of the elongated member 26. For instance, it may be desired that the distal tip 24 has a given width that is larger than the diameter of the elongated member 26 at the distal end 36 thereof, in which case the width of the proximal portion 34 of the distal tip 24 can be reduced to facilitate cooperation with the distal end 36 of the elongated member 26. Alternatively and as shown in FIG. 4, the width of the distal tip 24 can remain substantially the same throughout its length, and can thus have a width similar to the width of the distal end 36 of the elongated member 26.

In some implementations, the pivotable engagement of the distal tip 24 with the distal end 36 of the elongated member 26 can facilitate the magnetic interaction of the distal tip 24 with a magnetic implant, by enabling the distal tip 24 to deviate from the longitudinal axis of the elongated member 26 to get closer to the wall of the organ of the digestive tract. The pivotable engagement of the distal tip 24 with the distal end 36 of the elongated member 26 can also enable movement of the distal tip 24 relative to the elongated member 26 so that the distal tip 24 can adjust and/or conform to the variability in the outer surface of the small intestine, for instance, or another organ of the digestive tract.

In both FIGS. 3 and 4, the distal tip 24 includes a distal portion 40 that has rounded corners to give the oblong shape to the distal tip 24. The rounded corners can contribute to avoiding traumatic contact with the wall of the digestive tract when the distal tip 24 is navigated within the digestive tract, and when the distal tip 24 is navigated within the abdominal cavity of the patient.

The length of the distal tip 24 can also vary, and can be influenced for instance by the desired range of motion of the distal tip 24. For instance, the longer the length of the distal tip 24, the longer the arc length can be, thus enabling a wider range of motion of the distal tip 24. FIG. 3 illustrates an example of a distal tip 24 that has a longer length compared to the distal tip 24 illustrated in FIG. 4.

Figure 6:
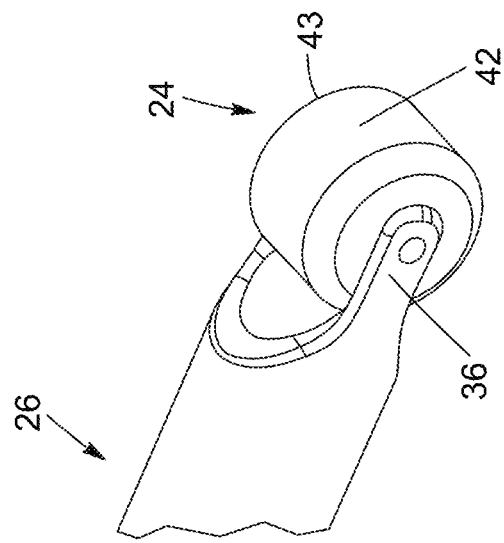
FIG. 6 is an enlarged view of a portion of a positioning wand showing another example of a distal tip of the positioning wand.
Figure 5:
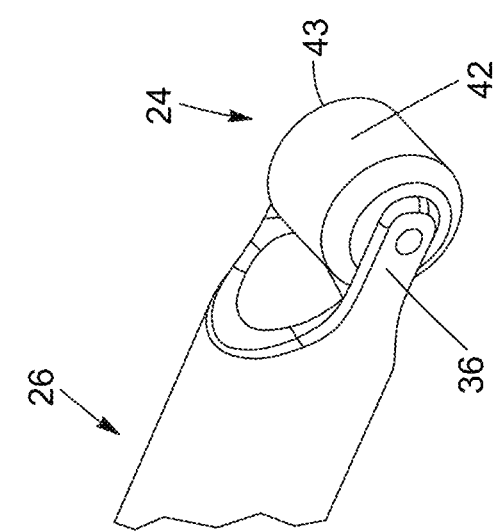
FIG. 5 is an enlarged view of a portion of a positioning wand showing another example of a distal tip of the positioning wand.
Figure 7:
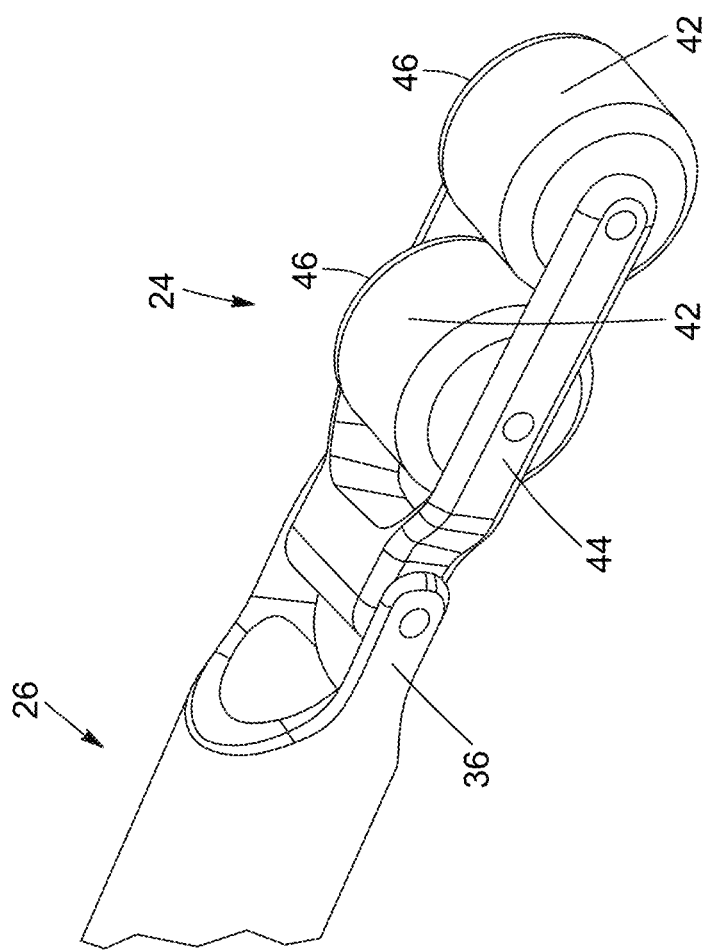
FIG. 7 is an enlarged view of a portion of a positioning wand showing another example of a distal tip of the positioning wand.

In other implementations, the distal tip 24 can have a cylindrical shape such as shown in FIGS. 5 to 7. In the implementations shown in FIGS. 5 and 6, the distal tip 24 has a cylindrical shape with a longitudinal axis, or central axis, that extends substantially perpendicular to the longitudinal axis of the elongated member 26. The distal tip 24 is pivotally engaged with the distal end 36 of the elongated member 26 via its central axis, such that the distal tip 24 can rotate up to 360° relative to the pivot axis. Accordingly, in such implementations, the distal tip 24 can be viewed as a wheel-type distal tip, and the distal tip 24 can be defined as being pivotally engaged with the elongated member 26, or rotatably engaged with the elongated member 26. A wheel-type distal tip can contribute to facilitating insertion and navigating into the digestive tract and abdominal cavity by enabling the outer surface 42 of the cylinder 43 to roll, or rotate, against the outer wall of the organ of the digestive tract or against various surfaces in the abdominal cavity, thereby reducing friction between the outer surface 42 of the cylinder 43 and the outer wall of the organ of the digestive tract or the various surfaces in the abdominal cavity, and reducing the sliding motion of the distal tip 24 against the outer wall of the organ of the digestive tract. Thus, in implementations where the distal tip 24 comprises a wheel-type distal tip, the surface of the wheel can roll on the wall of the organ of the digestive tract, instead of sliding against it. As is illustrated in FIGS. 5 and 6, the diameter of the distal tip 24, when the distal tip 24 is shaped as a wheel-type distal tip, can vary and can be adapted in accordance with the intended application of the positioning wand 20.

FIG. 7 illustrates another exemplary implementation of the distal tip 24. In the implementation shown, the distal tip 24 includes a frame 44 pivotally engaged with the distal end 36 of the elongated member 26. The frame 44 is configured to receive two cylindrical bodies 46, each one of the cylindrical bodies 46 being pivotally engaged with the frame 44. In this implementation, the frame 44 can thus rotate relatively to the elongated member 26, similarly to the distal tip 24 illustrated in FIGS. 3 and 4, and the cylindrical bodies 46 can rotate relative to the frame 44. This configuration of the distal tip 24 enables the distal tip 24 to have a range of motion along the arc length resulting from the rotation of the frame 44 relative to the elongated member 26, and can reduce friction between the respective outer surfaces 42 of the cylindrical bodies 46 and the outer wall of the organ of the digestive tract or the various surfaces in the abdominal cavity.

Figure 8:
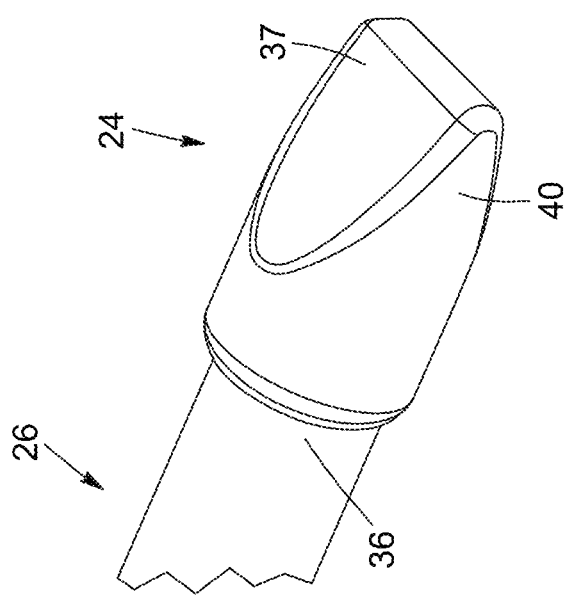
FIG. 8 is an enlarged view of a portion of a positioning wand showing another example of a distal tip of the positioning wand.
Figure 9A:
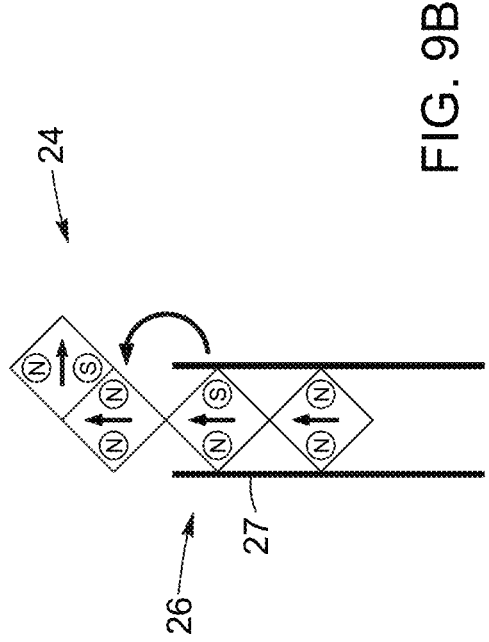
FIG. 9A-9D are side views of a distal tip that includes multiple magnets, the distal tip unfolding to form a polygonal shape without a void space.
Figure 9B:
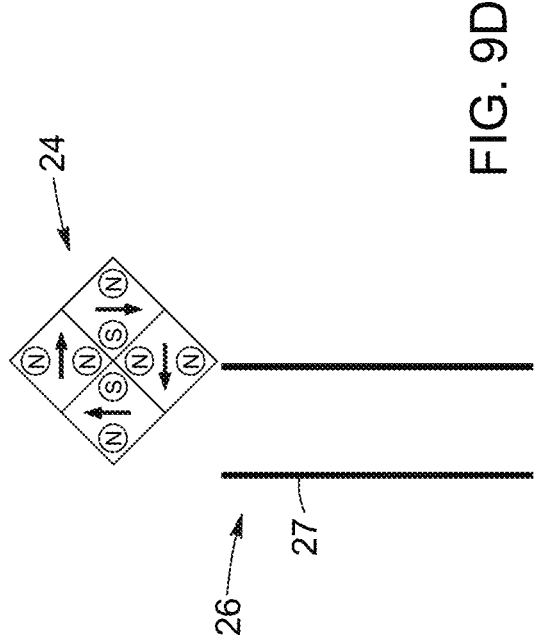
Figure 9C:
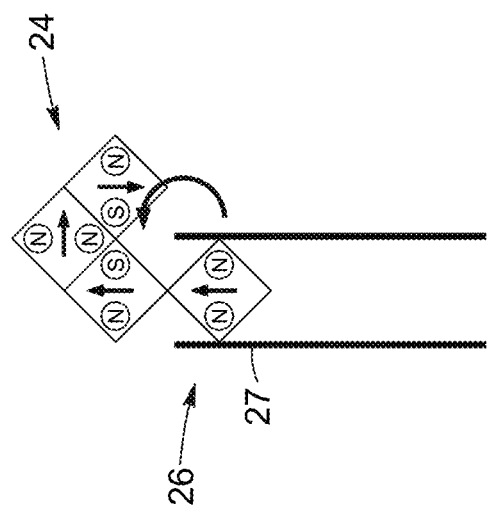
Figure 9D:
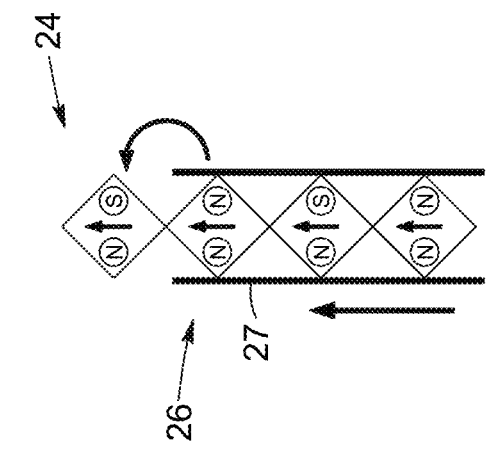

FIG. 8 illustrates yet another exemplary implementation of a distal tip 24. In this implementation, the distal tip 24 has a wedge shape and is fixedly engaged with the distal end 36 of the elongated member 26. In FIG. 8, the wedged portion 37 is provided at a distal end 40 of the distal tip 24. The wedge shape of the distal tip 24 can provide a wider surface area for the distal tip 24 to slid along the wall of the digestive tract, thereby reducing potential trauma to the tissues, such as the wall of the bowel.

In some implementations, the distal tip 24 can be engaged with the elongated member 26 via a spherical swiveling joint.

In some implementations, the distal tip 24 can be engaged with the distal end of the elongated member 26 via a biasable connection. The biasable connection can include for instance a spring, or a biasable neck extending between the distal end 36 of the elongated member 26 and the distal tip 24.

In yet other implementations, the distal end 36 of the elongated member 26 can include a grabber (not shown), and the grabber can be configured to grab a guide magnet. In such implementations, the guide magnet can have any of the configurations described herein, with the modification that the guide magnet can be releasably engageable with the grabber of the elongated member. As mentioned above, a control mechanism can be provided in the handle 22 of the positioning wand 20 to enable release of the distal tip 24, for instance when the distal tip 24 is graspable by the distal end 36 of the elongated member 26.

In some implementations, the distal tip 24 can be sized and configured to be received within the channel defined by the elongated member 26, such that the distal tip 24 can alternate between a retracted configuration and a deployed configuration. In such implementations, the distal tip 24 can be provided at a distal end of a guide wire or a longitudinally extending instrument provided within the channel of the elongated member 26. In the retracted configuration, the distal tip 24 can be received within the elongated member 26, for instance while the elongated member 26 is navigated to a certain location within the abdominal cavity. In the deployed configuration, the distal tip 24 can be located outside of the channel of the elongated member 26, at the distal end 36 thereof, such that the distal tip 24 protrudes or extends outwardly from the distal end 36 of the elongated member 26. It is to be understood that the reference to a deployed configuration of the distal tip 24 includes configurations where the distal tip 24 is partially deployed from the distal end 36 of the elongated member 26. When the distal tip 4 is provided at a distal end of a guide wire or a longitudinally extending instrument, the connection between the distal tip 24 and the distal end of the guide wire or the longitudinally extending instrument can be similar to the connection between the distal tip 24 and the elongated member 26 described above with respect to FIGS. 3 to 8. For instance, the distal tip 24 can be pivotally engaged with the distal end of the guide wire or the longitudinally extending instrument. Alternatively, the distal tip 24 can be fixedly engaged with the distal end of the guide wire or the longitudinally extending instrument.

As mentioned above, the distal tip 24 of the positioning wand 20 is configured to magnetically interact with a magnetic implant 12, 14 such as the ones illustrated in FIG. 1. The cooperation between the distal tip 24 of the positioning wand 20 and the magnetic implant can be enabled by the magnetic coupling of the distal tip 24 with the magnetic implant through a wall of an organ of the digestive tract. Once the distal tip 24 and the magnetic implant are magnetically coupled, the manipulation of the positioning wand 20 by the health care provider can enable the displacement of the magnetic implant to the desired site of the anastomosis via the magnetic interaction with the distal tip 24 of the positioning wand 20.

In order to do so, the distal tip 24 of the positioning wand 20 can include a guide magnet that is optionally received in a housing. The guide magnet can be any type of suitable magnet composed of the appropriate material. Examples of materials include neodymium magnets (e.g., NdFeB magnets), rare earth magnets, ferromagnetic magnets, and magnets made of a permanent magnetic material such as nickel and cobalt. A magnetically attracted ferrous metal core may take the place of a permanent magnet in the distal tip 24. In some implementations, the magnet or magnets of the distal tip 24 may be made of a magnetic material that is not permanently magnetized, such as soft magnetic alloys, e.g., nickel-iron, silicon iron, iron, iron-cobalt, and ferritic stainless steels.

In some implementations, the guide magnet can be made of an electromagnet, i.e., a magnet that is magnetic when subjected to an electric current. When the distal tip 24 includes an electromagnet, the electromagnet can be combined with an electric circuit that provides a variable magnetic strength to the electromagnet. For instance, the magnetic strength of the electromagnet can vary from no magnetic strength, e.g., when no magnetic interaction with the magnetic implant is desired, to a magnetic strength that enables sufficient magnetic interaction of the distal tip 24 with the magnetic implant to move the magnetic implant to the desired site of the anastomosis.

In some implementations, the interaction between the handle 22 and the elongated member 26 can enable the distal tip 24 to be deployed so as to control the magnetic interaction with the magnetic implant located within a lumen of the digestive tract. In other words, the extent of the deployment of the distal tip 24 can be such that the magnetic interaction with the magnetic implant is increased or decreased.

In some implementations, the guide magnet of the distal tip 24 can be configured such that its magnetic poles are aligned through the length of the magnetic material, such that one pole of the magnet of the distal tip 24 can be magnetically coupled with an opposite pole of the magnetic implant when the distal tip 24 and the magnetic implant are brought in sufficiently close proximity, i.e., the pole of the distal tip 24 is opposed to the pole of the compression surface of the magnetic implant. The distal tip 24 interacts with the magnetic implant. For instance, when the distal tip 24 has a configuration as shown in FIGS. 3, 4 and 8, the South pole of the magnet can be located at the distal portion 40 of the distal tip 24 and the North pole of the magnet can be located at the proximal portion 34 of the distal tip 24, while the magnet of the magnetic implant can be configured such that the North pole is located on the compression surface side of the magnetic implant, while the South pole is located on the lumen-oriented side of the magnetic implant. With such a configuration of the respective magnets of the distal tip 24 and of the magnetic implant, the South pole of the distal tip 24 can magnetically couple with the North Pole of the magnetic implant through the wall of the organ of the digestive tract along which the magnetic implant is displaced. Of course, the reverse configuration of the magnetic poles is also possible.

When the distal tip 24 is configured as a wheel-type distal tip as shown in FIGS. 5 to 7, the magnet can be for instance a non-permanent magnet, a magnetic core, or a soft magnetic material.

In some implementations, the guide magnet of the distal tip 24 can include a plurality of magnets. The plurality of magnets can be provided as a linear chain of magnetic segments that are hingedly connected with each other via a hinge, a wire, a chain, or an exoskeleton. In some implementations, the hinged connection between adjacent magnets can enable the plurality of magnets to self-assemble into a square, hexagon, octagon, or another geometry.

When the guide magnet includes a plurality of magnets, the polarity of the magnets can be chosen to achieve a certain configuration of the assembly of magnets once the plurality of magnets is deployed, or partially deployed, out of the elongated member 26. For instance, the plurality of magnets can include magnets having a S-S polarity, a N-S polarity, a S-N polarity, or a N-N polarity. When the plurality of magnets includes magnets that are provided successively as a linear train, the succession of magnets can alternate between a magnet having a N-N polarity or S-S polarity with a magnet having a S-N polarity or N-S polarity such that magnets having complimentary polarities can magnetically couple to achieve a resulting magnet having a given shape. For instance, with reference to FIG. 9, the plurality of magnets can include four magnets initially provided as a linear train within the channel of the elongated member 26 (top left), and as the magnets are released from the elongated member 26, adjacent magnets magnetically couple in accordance with their respective polarity to form a resulting square-shaped magnet corresponding to the distal tip 24.

The magnet or the plurality of magnets of the distal tip 24 can be received in a housing. When the magnet includes a plurality of magnets, the plurality of magnets can be received in a single housing. When the plurality of magnets is received in a single housing, the single housing can be flexible. The plurality of magnets received in the flexible housing can be connected via a hinged connection, or can be provided in a spaced apart relationship within the housing. The hinged connection or the space between adjacent magnets can enable a movement of the magnets relative to each other, particularly when the single housing is a flexible housing. Providing multiple magnets within a single housing can thus contribute to enhancing the flexibility of the distal tip 24, such that it can become easier to bend when subjected to a force. Alternatively, each one of the magnets of the plurality of magnets can be received in a corresponding housing. The corresponding housings can be provided as a linear chain of magnetic segments that are hingedly connected with each other via a hinge, a wire, a chain, or an exoskeleton. In some implementations, the magnet can be partially housed in a housing, with a portion of the magnet is received in the housing while another portion is free of housing.

The housing can be made of various materials. In some implementations, the housing can be made of a biocompatible polymeric material or of a metallic material. Examples of suitable polymeric materials include silicones, e.g., polydimethylsiloxane; or a fluoropolymer, e.g., polytetrafluoroethylene, conformable polymers, or any other type of medical implant grade polymers. Examples of metallic materials can include a titanium alloy, cobalt chromium, an austenitic stainless steel, or any other type of medical implant grade metals.

The housing can include a surface that is smooth and lubricious. The surface that is smooth and lubricious can be the surface that may be in contact with the wall of the organ of the digestive tract into which the magnetic implant has been delivered to the site of the desired anastomosis, which can contribute to reducing friction between the housing and the wall of the digestive tract or the various surfaces in the abdominal cavity.

The housing can also provide a protective coating around the magnet or the plurality of magnets to prevent corrosion.

The housing can include additional features, such an engagement mechanism enabling connection of the distal tip 24 to the elongated member 26. In some implementations, the engagement mechanism can be such that the distal tip 24 is released from the elongated member 26. The engagement mechanism can be such that the distal tip 24 is connected to the elongated member 26 or to a guide wire or a longitudinally extending instrument received in a channel of the elongated member 26. The engagement mechanism can refer to the cooperation of a connecting member, or tether, of the distal tip 24 with a connector of the elongated member 26, or with the guide wire or the longitudinally extending instrument received in the channel of the elongated member 26.

In some implementations, the connecting member can include a pommel snare, also referred to as a knob feature. In such implementations, the guide wire or the longitudinally extending instrument can be loaded into the channel of the elongated member 26, and the distal tip 24 can be releasably attached to the distal end 36 of the elongated member 26 via a snare as the connector, the snare being wrapable around the pommel snare, or knob feature, of the distal tip 24. The distal tip 24 can be docked onto the elongated member 26 by applying tension to the snare wire relative to the elongated member 26 and by locking the snare wire relative to the elongated member 26 using a handle set positioned at the proximal end of the elongated member 26 of the positioning wand 20. The pommel snare of the distal tip 24 can be located in a middle portion or at a distal end thereof for instance.

In some implementations, the connecting member can be a loop, and the connector can be a grabber that includes a U-shaped jaw. The grabber can be advanced distally relative to the elongated member 26 so that the loop can be released from the U-shaped jaw of the grabber. The connector can also be a mechanically actuated jaw grabber that can be used to grab the loop instead of the grabber that includes a U-shaped jaw. The mechanically actuated jaw grabber includes a slot cut through it to accept the loop, and can pull the loop into the elongated member 26 to retract or deploy the distal tip 24. The loop can be made of a biocompatible braided wire, solid wire, or nitinol wire. It can also be made of a biocompatible monofilament or a braided polymer line. The connecting member can be a ball, and the connector can be a mechanically actuated jaw that includes a slot feature configured to receive the ball therein.

In the implementations described above, it is to be understood that the connecting member of the distal tip 24 can form part of the housing, or can alternatively form part of the magnet when no housing is present. It is also to be understood that other types of connector and connecting member can also be suitable to enable engagement of the distal tip 24 with the elongated member 26.

The housing 16 of the distal tip 24 can be larger than the magnet to distribute the magnetic force over a larger area. The housing of the distal tip 24 can be made of a single piece, or be formed of multiples pieces. For instance, the housing can include two portions coupled at a parting line where they mate together once assembled. The parting line may be incorporated anywhere along the thickness of the magnetic implant. This clamshell construction allows for easy assembly and encapsulation of the component parts that reside within the housing, such as the magnet. The housing and its internal components may be bonded together using adhesives or thermally reflowed or overmolded if the housing is formed of a thermoplastic resin. If the housing is made of a metallic material, the parting line of the top and bottom housing may be laser welded to bond the housing together and create a hermetic seal around the magnetic core, or magnet. Alternatively, the housing can be one integral body if formed using molding techniques.

In some implementations, the distal tip 24 can incorporate a sensor configured to detect a magnetic field strength. In some implementations, the sensor can include a giant magnetoresistance (GMR) sensor. The sensor can facilitate guiding the positioning wand 20 to the location of the magnetic implant when navigating the abdominal cavity of the patient. Alternatively, the sensor can be provided at a distal end of an endoscope used to aid in placement of the magnetic implants. In yet other implementations, the sensor can be provided on an instrument located outside the body of the patient, and manipulated by a health care provider to facilitate the positioning of the magnetic implants.

The sensor can be operatively connected to a monitor that displays the changes in magnetic field, expressed in amperes per meter (A/m) or in Oersteds (Oe), for instance. For example, in an implementation where a first magnetic implant 12 is delivered in a distal portion of the digestive tract and a second magnetic implant 14 is delivered in a proximal portion of the digestive tract, the sensor can be provided on the positioning wand 20 that interacts with the first magnetic implant 12, or can be provided on a delivery catheter to interact with the second magnetic implant 14. The sensor can be configured to zero out the magnetic field of the first magnetic implant 12, and when brought in proximity to the second magnetic implant 14, the sensor can detect the magnetic field of the second magnetic implant 14 and provide information about the variations in magnetic field as the first magnetic implant 12 is moved. The sensor can also detect, based on the magnetic field, whether the first and second magnetic implants 12, 14 are correctly aligned and docked to each other. For instance, when the first and second magnetic implants 12, 14 are correctly aligned, the magnetic field displayed will typically be at its highest, indicating that the placement of the first and second magnetic implants 12, 14 for forming the anastomosis has been successful.

Method for Assisting in the Deployment of Magnetic Implants for Forming an Anastomosis in the Digestive Tract A method for assisting in the deployment of magnetic implants used for forming an anastomosis between two adjacent walls of a digestive tract of a patient using the positioning wand as described herein will now be described in further detail.

The method can include delivering a first magnetic implant into the digestive tract of a patient to a first location, on one side of a desired anastomose site, within the lumen of a first hollow organ, and delivering a second magnetic implant into the digestive tract of the patient to a second location on another side of the desired anastomose site, within the lumen of a second hollow organ.

Various techniques can be used to deliver the first and second magnetic implants. It is to be noted that a chosen technique for delivering the first magnetic implant can be the same or different of the chosen technique for delivering the second magnetic implant. In some implementations, the delivery of the magnetic implants can be performed via a natural cavity of the patient, i.e., the mouth or the anus, using for example an endoscopic device. In some implementations, delivering the first and second magnetic implants can include releasably engaging the first and second magnetic implants with a corresponding delivery catheter insertable in a working channel of a corresponding endoscope.

Then, the positioning wand as described herein can be used to facilitate the navigation of at least one of the first and second magnetic implants to the desired site of the anastomosis, such that the first and second magnetic implants can be aligned to be magnetically coupled.

In order to do so, the distal tip and at least a portion of the elongated member of the positioning wand can be inserted in the abdominal cavity of the patient via any suitable procedure. In some implementations, the distal tip and the at least a portion of the elongated member of the positioning wand can be inserted into the abdominal cavity of the patient using a minimally invasive surgery, or via a natural orifice. Minimally invasive surgeries can include laparoscopic surgeries, which typically include cooperation with a trocar to facilitate introduction of a laparoscopic instrument into the abdominal cavity. Alternatively, the laparoscopic surgery can be a percutaneous laparoscopy, which can enable introduction of the distal tip and the at least a portion of the elongated member of the positioning wand into the abdominal cavity without the use of a trocar. The distal tip and the at least a portion of the elongated member of the positioning wand can also be inserted into the abdominal cavity of the patient by performing a NOTES procedure.

Once the distal tip and the at least a portion of the elongated member of the positioning wand are within the abdominal cavity of the patient, the health care provider can move the distal tip and the at least a portion of the elongated member towards the at least one of the magnetic implants for which placement to the desired site of the anastomosis is required, via the handle of the positioning wand, such that the distal tip is brought in sufficiently close proximity to the at least one magnetic implant to enable magnetic coupling therebetween. It is to be understood that as the magnetic implant is provided within the lumen of the hollow organ and the distal tip is within the abdominal cavity of the patient but outside of the lumen of the hollow organ, the wall of the hollow organ is sandwiched between the magnetic implant and the distal tip following their magnetic coupling.

In some implementations, bringing the distal tip of the positioning wand and the magnetic implant in sufficiently close proximity can involve translating, or sliding, the first magnetic implant within the lumen of the first hollow organ, for instance along a wall thereof, to align the first magnetic implant with the second magnetic implant that is in the lumen of the second hollow organ. In some implementations, bringing the distal tip of the positioning wand and the first magnetic implant in sufficiently close proximity can involve rotating the first magnetic implant within the lumen of the first hollow organ, for instance along a wall thereof, to align the first magnetic implant with the second magnetic implant that is in the lumen of the second hollow organ.

In some implementations, bringing the distal tip of the positioning wand and the magnetic implant in sufficiently close proximity can involve translating, or sliding, the second magnetic implant within the lumen of the second hollow organ, for instance along a wall thereof, to align the second magnetic implant with the first magnetic implant that is the lumen of the first hollow organ. In some implementations, bringing the distal tip of the positioning wand and the magnetic implant in sufficiently close proximity can involve rotating the second magnetic implant within the lumen of the second hollow organ, for instance along a wall thereof, to align the second magnetic implant with the first magnetic implant that is the lumen of the first hollow organ.

The positioning wand can thus be used to manipulate and position either one of the first magnetic implant or the second magnetic implant, or both, to enable magnetic coupling between the first and second magnetic implants.

In other implementations, bringing the distal tip and the magnetic implant in sufficiently close proximity can involve displacing the hollow organ into which is received the magnetic implant, or moving a region of the digestive tract containing one of the magnetic implants to a location near the desired site of the anastomosis. For instance, the first hollow organ into which is received the first magnetic implant can be a proximal portion of the small intestine, and the second hollow organ into which is received the second magnetic implant can be a distal portion of the small intestine. In order to bring the first and second magnetic implants in sufficiently close proximity to enable their magnetic coupling, the distal tip of the positioning wand can magnetically interact with the second magnetic implant to bring the distal portion of the small intestine in sufficiently close proximity to the proximal portion of the small intestine where is located the first magnetic implant such that the first and second magnetic implants can magnetically couple. Following the magnetic coupling of the first and second magnetic implants, the distal portion of the small intestine can be maintained at the desired location of the anastomosis via the magnetic force between the first and second magnetic implants.

Furthermore, it is to be noted that additional standard surgical instruments such as graspers and forceps can be used to facilitate moving a portion of the digestive tract near another portion of the digestive tract.

The attractive magnetic force between the distal tip of the positioning wand and the magnetic implant and through the wall of the hollow organ into which is received the magnetic implant is sufficiently strong to enable manipulation of the magnetic implant via a sliding motion, and/or to displace a region of the digestive tract to another. The attractive magnetic force between the distal tip and the magnetic implant and through the wall of the hollow organ into which is received the magnetic implant is such that the tissue of the hollow organ retains its integrity and is not permanently damaged by the magnetic compression between the distal tip and the magnetic implant, either while stationary or while sliding the magnetic implant. In addition, the attractive magnetic force between the distal tip and the magnetic implant and through the wall of the hollow organ into which is received the magnetic implant is such that magnetic uncoupling can be achieved when the magnetic implant has successfully reached the desired site of the anastomosis.

In some implementations and as mentioned above, the distal tip can be releasable from the elongated member of the positioning wand. In such implementations, the distal tip of the positioning wand can be magnetically coupled with a first magnetic implant. The distal tip is then released from the elongated member while remaining coupled therewith, for instance via a guide wire. Releasing the distal tip from the elongated member while maintaining the magnetic coupling between the distal tip and the first magnetic implant can enable the elongated member to be moved to another location within the abdominal cavity of the patient. Once the elongated member has been moved to a different location within the abdominal cavity of the patient, the guide wire can be retracted back into the elongated member to move the region of the digestive tract where the magnetic coupling of the distal tip and the first magnetic implant has occurred, to another region that is in sufficiently close proximity to the second magnetic implant for the first and second magnetic implants to magnetically couple. Alternatively, the distal tip and guide wire can both be released from the elongated member, and the guide wire can be subsequently grasped and pulled by a second instrument to move the region of the digestive tract where the magnetic coupling of the distal tip and the first magnetic implant has occurred, to another region that is in sufficiently close proximity to the second magnetic implant for the first and second magnetic implants to magnetically couple.

Once the magnetic implants have been delivered within their respective hollow organ and on their respective side the of the desired anastomosis, the first and second magnetic implants can be brought in sufficiently close proximity to enable magnetic coupling of the first and second magnetic implants through the two adjacent vessel walls of the digestive tract, such that the compression surface of each of the first and second magnetic implants contacts the interior wall of their respective hollow organ at the site of the desired anastomosis. The magnetic coupling of the two magnetic implants compresses a portion of the two adjacent walls therebetween, and the portion that is compressed between the respective compression surfaces of the magnetic implants eventually forms a necrotic area as the blood flood supply to this area progressively declines.

In some implementations, the first and second magnetic implants can be manipulated by using a magnet externally, for instance to facilitate the passing of the coupled magnetic implants via the bowel lumen of the patient. An endoscope can also be used to manipulate the coupled magnetic implants internally, also to facilitate their passing via the bowel lumen of the patient.

In some implementations, one or more positioning wand as described herein can be used in combination with other laparoscopic, transluminal, or endoscopic devices.

In addition, one or more magnetic or non-magnetic laparoscopic or endoscopic clips can be deployed near the intended locations of one or more magnetic implants such that the clips can serve as temporary markers for the intended locations. In such scenarios, the positioning wand can be manipulated by the health care provider to engage mechanically or magnetically with the clips, which can facilitate confirming that the positioning wand, and more particularly the distal tip of the positioning wand, has reached the intended location. The clips may also serve as "handles" for attaching the distal tip of the positioning wand or other surgical instruments, such as mechanical graspers, to move regions of the gastrointestinal tract.

In some implementations, the distal tip that is magnetically coupled with the first magnetic implant can be used to hold a region of the digestive tract in place during other another surgical procedure.

Referring now to FIGS. 10 to 16, various examples of the above described method will be described in further detail.

Figure 10:
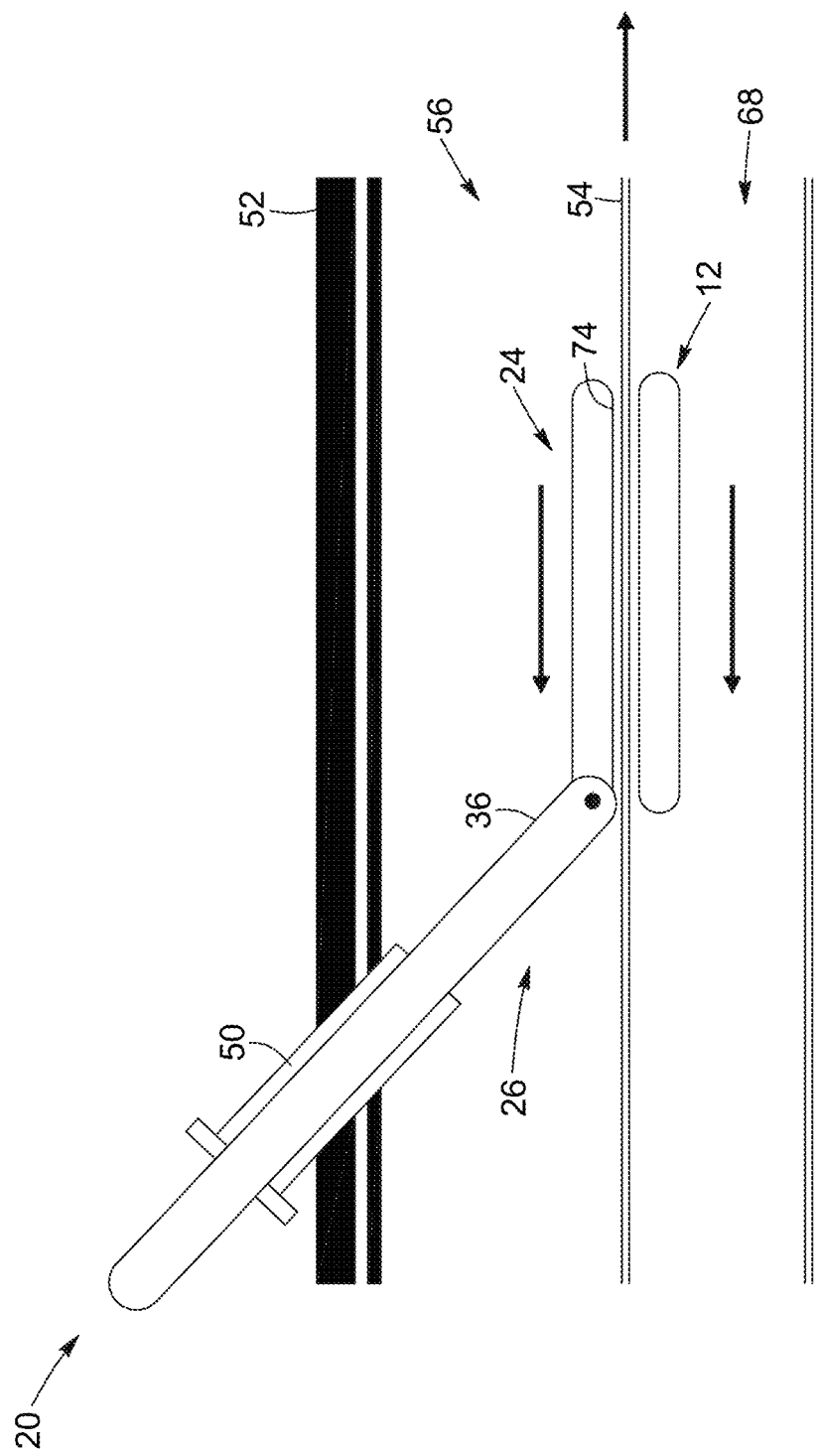
FIG. 10 is a side view of a positioning wand and a magnetic implant, the positioning wand including an elongated member and a distal tip, a portion of the elongated member and the distal tip being shown in an abdominal cavity, and the magnetic implant being shown in a lumen of an organ of the digestive tract.

FIG. 10 illustrates an implementation wherein a laparoscopic trocar 50 is inserted through the abdominal wall 52 of a patient, with the elongate member 26 being inserted through the opening of the laparoscopic trocar 50 and into the abdominal cavity 56. In this implementation, the positioning wand 20 includes an elongated member 26 and a distal tip 24 as shown in FIGS. 3 and 4 and as described above. The distal tip 24 is hingedly connected to the distal end 36 of the elongate member 26, for instance via a hinge pin. The distal tip 24 can pivot about a hinge axis, thereby enabling the distal tip 24 to conform to an outer surface of the wall 54 of a body lumen, i.e., the outer surface of an organ of the digestive tract. The magnetic implant 12 is positioned within the lumen 68 of the organ of the digestive tract, such as the lumen of the bowel. The distal tip 24 is magnetically attracted to the magnetic implant 12 through the wall 54 of the organ of the digestive tract. The shape and material selection of the distal tip 24 is designed such that the magnetic attraction force between the distal tip 24 and the magnetic implant 12 is sufficient to enable translating, or dragging, the magnetic implant 12 within the lumen 68 of the organ of the digestive tract while minimizing the pressure on the outer surface of the wall 54 of the organ of the digestive tract, to prevent damage to the wall 54 of the organ. The magnetic implant 12 is thus translated within the bowel by moving the distal tip 24 relative to the outer surface of the wall 54 of the organ of the digestive tract.

In some implementations, the organ into which is received the magnetic implant 12 can be held in position with a secondary laparoscopic grasper tool while the distal tip 24 is being translated in the opposite direction. Alternatively, the magnetic implant 12 can be translated by fixing the distal tip 24 and by translating the organ with the secondary laparoscopic grasper tool.

Figure 11B:
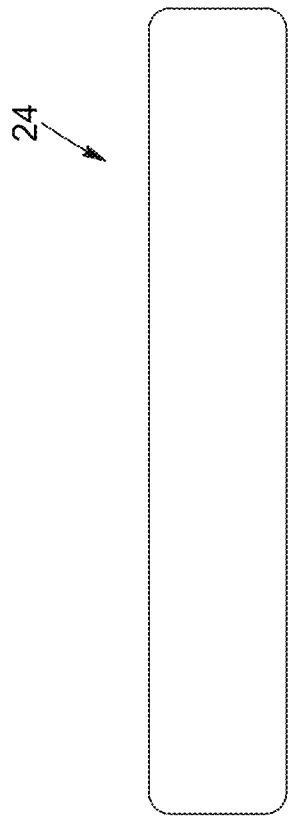
FIG. 11B is a top view of the distal tip of FIG. 11A.
Figure 11C:
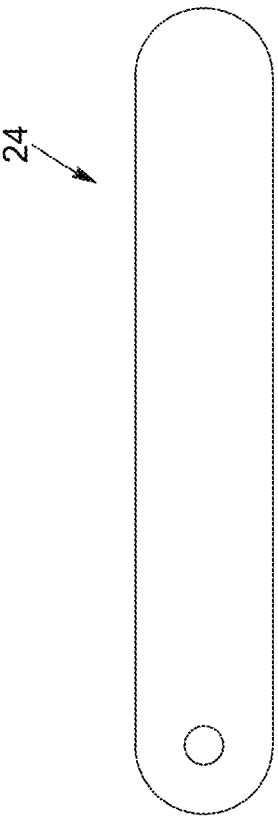
FIG. 11C is a side view of the distal tip of FIG. 11A.
Figure 11A:
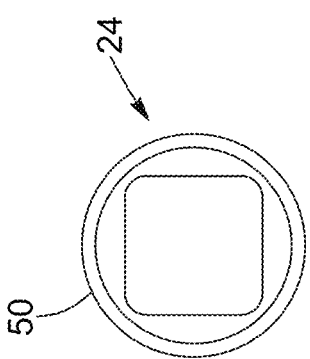
FIG. 11A is a front view of a distal tip of a positioning wand shown in relation with a trocar.

As mentioned above, the size and shape of the distal tip 24 can be determined to enable insertion through the opening of a trocar 50, while having a sufficiently large surface area to provide enough attractive magnetic force to translate or drag the magnetic implant 12. In addition, the interface of the distal tip 24 that interacts with the wall 54 of the organ can be chosen to be large enough to minimize the pressure exerted on the wall 54 of the organ. Accordingly, the distal tip 24 can be configured to be conformable to the wall 54 of the organ, such as the outer surface of the bowel. A distal tip 24 having an elongated shape, or that includes a series of elongated members, can also be beneficial for insertion through the opening of the trocar 50, such as shown in FIGS. 11A to 11O.

FIG. 10 illustrates the conformation of the distal tip 24 to the outer surface of the wall 54 of the organ of the digestive tract. The distal tip 24 has a wall-contacting surface 74 that contacts the outer surface of the wall 54 of the organ of the digestive tract, such that a larger portion of the wall-contacting surface 74 of the distal tip 24 contacts the outer surface of the wall 54 of the organ, while the longitudinal axis of the elongate member 26 can extend at a different angle relative to the distal tip 24. Without the hinged connection between the elongate member 26 and the distal tip 24, a smaller portion of the distal tip 24 would be in contact with the outer surface of the wall 54 of the organ, for instance the distal portion 40 of the distal tip 24, which can reduce the surface area of the magnetic interaction between the distal tip 24 and the magnetic implant 12, which in turn can have deleterious effect on the wall 54 of the organ by increasing the pressure at a specific point of contact.

Figure 12:
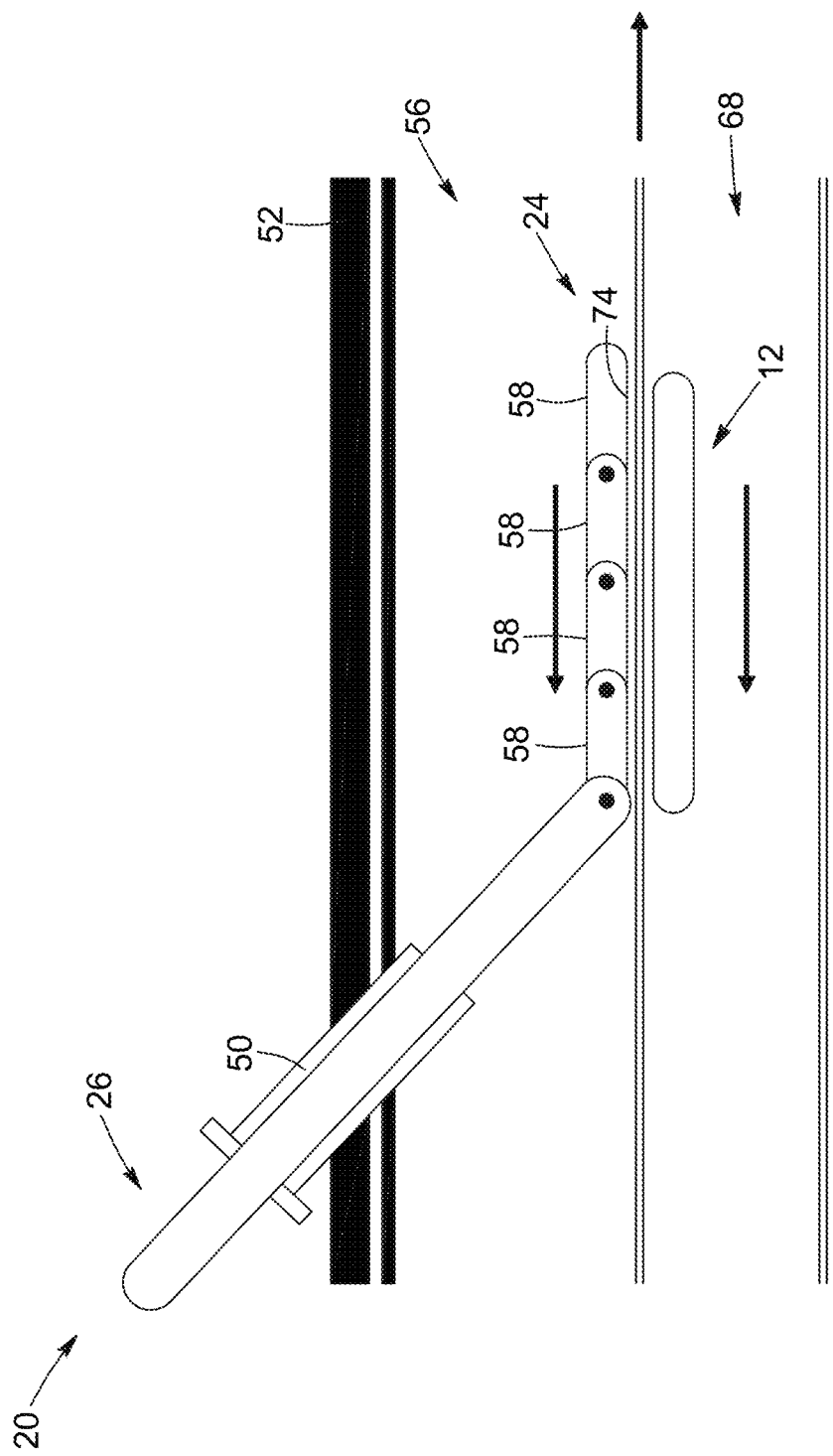
FIG. 12 is a side view of a positioning wand and a magnetic implant, the positioning wand including an elongated member and a distal tip including multiple segments, a portion of the elongated member and the distal tip being shown in an abdominal cavity, and the magnetic implant being shown in a lumen of an organ of the digestive tract.

Referring now to FIG. 12, there is shown an implementation of the distal tip 24 that includes multiple segments 58 that are hingedly connected via hinge pins, as well as being hingedly connected to the distal end 36 of the elongate member 26. In this implementations, the assembly of multiples segments 58 forms a flexible train, or chain, of distal tip elements that can be conformable to the outer surface of the wall 54 of the organ of the digestive tract, while being configurable at an angle relative to the longitudinal axis of the elongate member 26.

Figure 13:
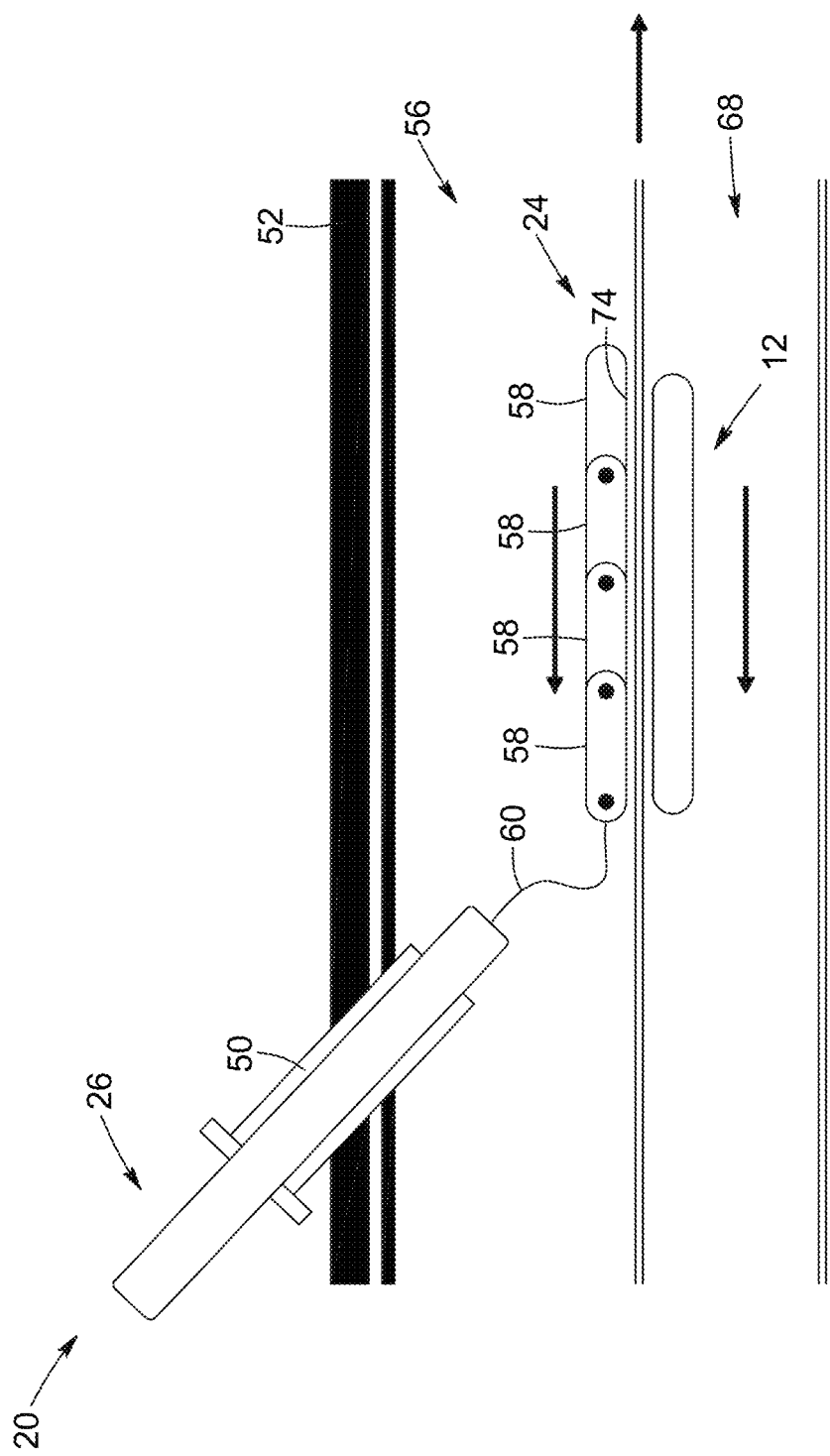
FIG. 13 is a side view of a positioning wand and a magnetic implant, the positioning wand including an elongated member and a distal tip including multiple segments, a portion of the elongated member and the distal tip being shown in an abdominal cavity and connected to each other with a flexible cable, and the magnetic implant being shown in a lumen of an organ of the digestive tract.

FIG. 13 illustrates an implementation that is similar to the implementation shown in FIG. 12, although in FIG. 13, the assembly of multiples segments 58 is connected to the elongate member 26 via a flexible cable 60 rather than a hinge pin. This type of connection between the distal tip 24 and the elongate member 26 enables multiplanar flexibility and conformability of the distal tip 24 to the magnetic implant 12 relative to the elongate member 26. In this implementation, the distal tip 24 can be configurable between a retracted configuration and a deployed configuration, for instance by manipulating the flexible cable 60, or guide wire, within the elongate member 26, such as by pulling on the flexible cable 60. For example, the retracted configuration can be used to introduce and remove the distal tip 24 from the abdominal cavity through the trocar 50.

Figure 14:
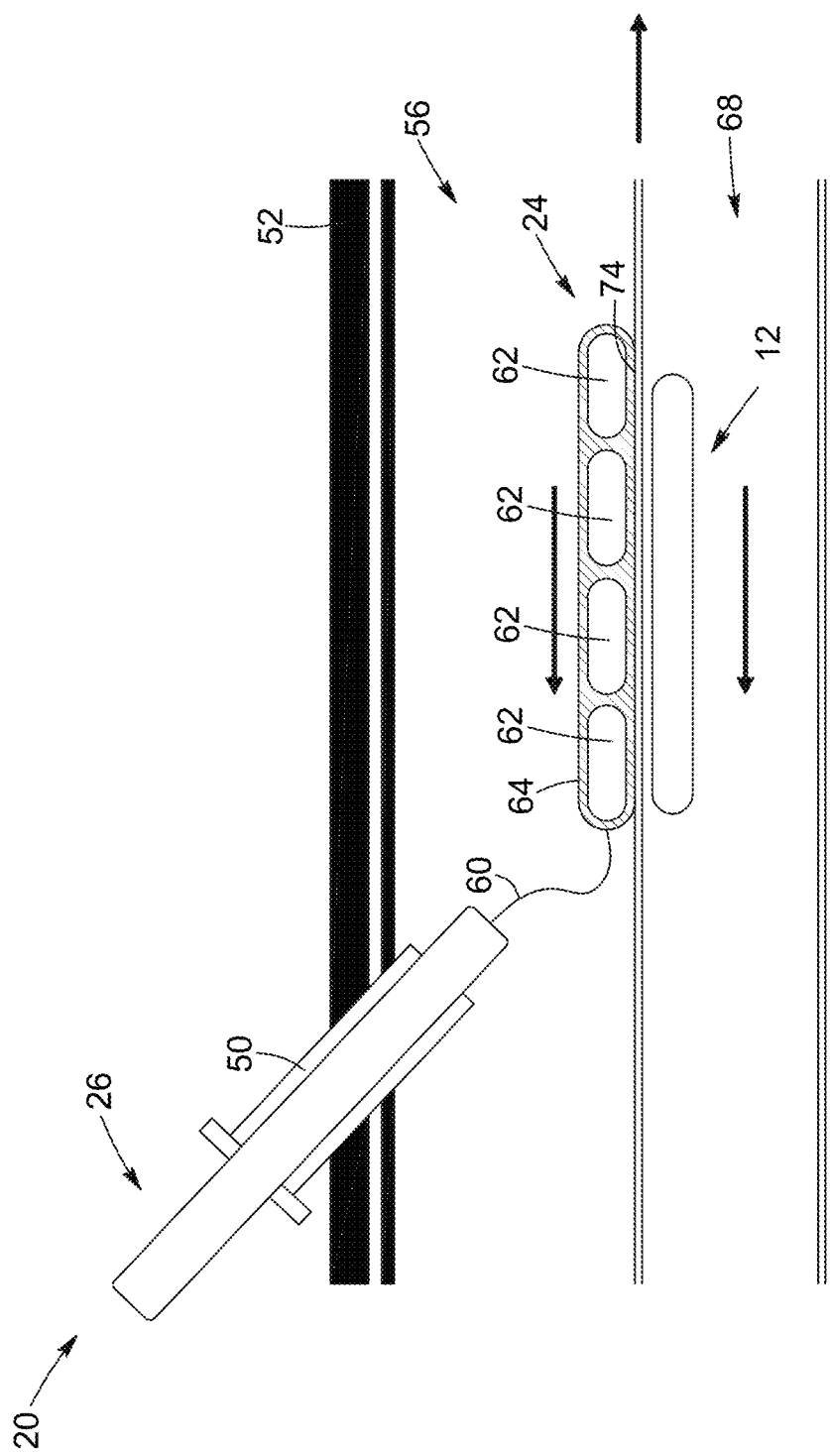
FIG. 14 is a side view of a positioning wand and a magnetic implant, the positioning wand including an elongated member and a distal tip including a plurality of magnets received in a housing, a portion of the elongated member and the distal tip being shown in an abdominal cavity, and the magnetic implant being shown in a lumen of an organ of the digestive tract.

FIG. 14 illustrates an alternative implementation, wherein the distal tip 24 includes a plurality of magnets 62 housed in a flexible housing 64. FIG. 14 thus illustrates an implementation wherein the plurality of magnets are received in a single housing, as described above.

Figure 15:
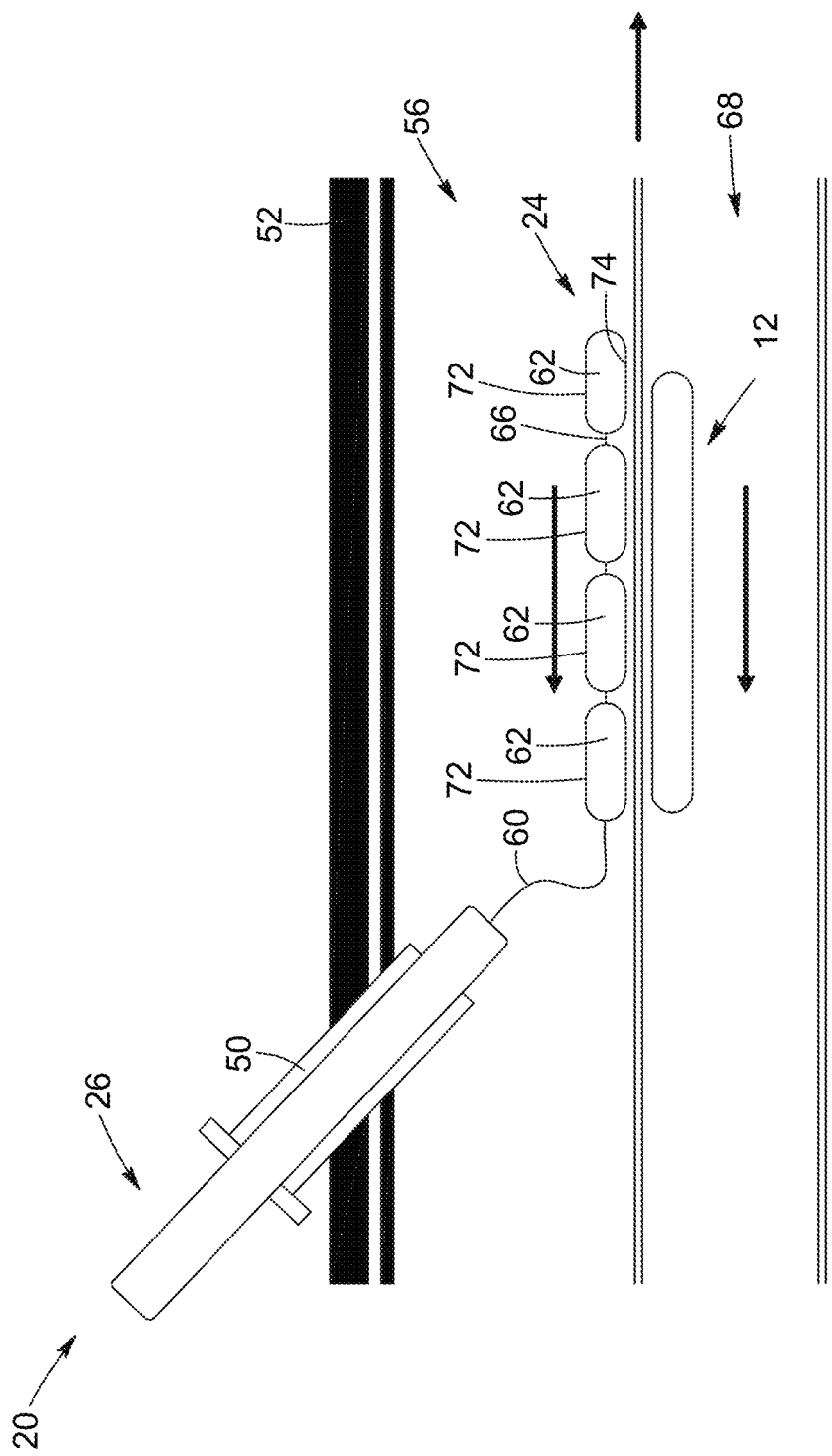
FIG. 15 is a side view of a positioning wand and a magnetic implant, the positioning wand including an elongated member and a distal tip including a plurality of magnets each received in a corresponding housing, a portion of the elongated member and the distal tip being shown in an abdominal cavity, and the magnetic implant being shown in a lumen of an organ of the digestive tract.

FIG. 15 illustrates yet another alternative implementation, wherein the distal tip 24 includes a plurality of magnets 62, with each magnet being optionally housed in a corresponding housing 72. The plurality of magnets 62 are connected in series via a wire 66, or chain, to provide flexibility to the assembly of magnets 62. This type of connection can enable the assembly of magnets 62 to be flexible in one or more planes and/or enable rotation of the magnets 62 with respect to one another.

Figure 16:
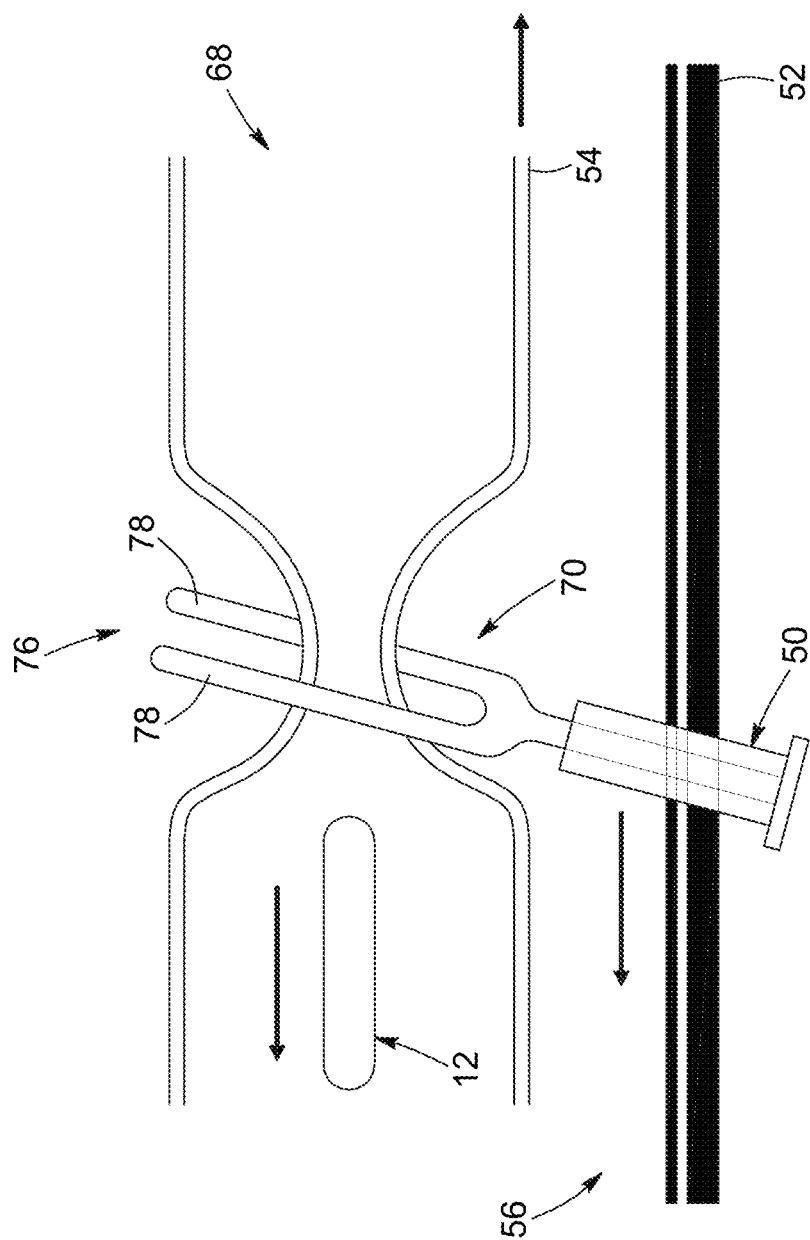
FIG. 16 is a side view of a secondary laparoscopic tool and a magnetic implant, a portion of the secondary laparoscopic tool and the distal tip being shown in an abdominal cavity, and the magnetic implant being shown in a lumen of an organ of the digestive tract.

Referring now to FIG. 16, there is shown an implementation of a secondary laparoscopic tool 70 and associated method to translate a magnetic implant 12 within a lumen 68 of an organ of the digestive tract, such as the bowel. The secondary laparoscopic tool 70 is introduced through the opening of a trocar 50 that is inserted into the abdominal cavity 56 through the abdominal wall 52. In the implementation shown, the secondary laparoscopic tool 70 has a distal end 76 that is tong-shaped and configured to grasp the wall 54 of the bowel proximal to the magnetic implant 12 so that the bowel is constrained in one plane to a dimension smaller than the cross-sectional profile of the magnetic implant 12. Once the bowel is compressed to a smaller size, the secondary laparoscopic tool 70 is moved distally to displace or translate the magnetic implant 12 within the lumen 68 of the bowel. The secondary laparoscopic tool 70 can have a distal end that has a fixed shape, or the branches 78 of the tong of the distal end 76 can be individually actuated to be configurable between an open configuration and a closed configuration. The bowel can be held in position with an additional grasper tool while the secondary laparoscopic tool 70 can be moved relative to the bowel. Conversely, the secondary laparoscopic tool 70 can be held in position while the bowel is moved with the additional grasper tool. Alternatively, both the secondary laparoscopic tool 70 and the additional grasper tool can be moved simultaneously.

In some implementations, the secondary laparoscopic tool 70 can be non-magnetic. The use of a secondary laparoscopic tool 70 that is non-magnetic can facilitate the interaction between the positioning wand 20 and the secondary laparoscopic tool 70, such that one of the positioning wand 20 and the secondary laparoscopic tool 70 is magnetically engaged with the magnetic implant. The secondary laparoscopic tool 70 can be used for instance to position a portion of the bowel at a given location within the abdominal cavity, and once that is done, the positioning wand 20 and the magnetic implant 12 can be manipulated to be magnetically coupled and be displaced to the desired site of the anastomosis.

Several alternative implementations and examples have been described and illustrated herein. The implementations of the technology described above are intended to be exemplary only. A person of ordinary skill in the art would appreciate the features of the individual implementations, and the possible combinations and variations of the components. A person of ordinary skill in the art would further appreciate that any of the implementations could be provided in any combination with the other implementations disclosed herein. It is understood that the technology may be embodied in other specific forms without departing from the central characteristics thereof. The present implementations and examples, therefore, are to be considered in all respects as illustrative and not restrictive, and the technology is not to be limited to the details given herein. Accordingly, while the specific implementations have been illustrated and described, numerous modifications come to mind.

The invention claimed is:

1. A positioning wand for assisting in positioning at least one of a first magnetic implant and a second magnetic implant configured for forming an anastomosis between two adjacent walls of a digestive tract of a patient, the positioning wand comprising:
an elongated member sized and configured to have at least a portion thereof to be inserted into an abdominal cavity of the patient; and
a distal tip engaged with a distal end of the elongated member and comprising a plurality of individual magnetic segments connected in series in an end-to-end fashion, the plurality of individual magnetic segments being configured to magnetically couple with the at least one of the first and second magnetic implants through a wall of the digestive tract to translate the at least one of the first and second magnetic implants along an inner surface of the wall of the digestive tract to a desired site of the anastomosis, the plurality of individual magnetic segments being configured for placement against an outer surface of the wall of the digestive tract to be moveable in response to a contact pressure upon contact with the outer surface of the wall of the digestive tract.

2. The positioning wand of claim 1, wherein the plurality of individual magnetic segments forms a flexible train conformable to the outer surface of the wall of the digestive tract.

3. The positioning wand of claim 1, wherein a distal end of a first one of the plurality of individual magnetic segments is hingedly connected to a proximal end of a second one of the plurality of individual magnetic segments via a hinge.

4. The positioning wand of claim 1, wherein the positioning wand further comprises a flexible wire for engaging a proximal one of the plurality of individual magnetic segments to the distal end of the elongated member.

5. The positioning wand of claim 1, wherein the distal tip is configured to be moveable in response to the contact pressure upon contact with the wall of the digestive tract to lighten the contact pressure.

6. The positioning wand of claim 1, wherein the elongated member includes at least one flexible portion and at least one rigid portion.

7. The positioning wand of claim 1, wherein the at least one of the first and second magnetic implants is an elongated magnetic implant.

8. The positioning wand of claim 1, wherein the plurality of individual magnetic segments connected in series is housed in a flexible housing.

9. The positioning wand of claim 1, wherein individual magnetic segments of the plurality of individual magnetic segments are spaced-apart from one another.

10. The positioning wand of claim 1, wherein individual magnetic segments of the plurality of individual magnetic segments are partially overlapping each other.

11. The positioning wand of claim 1, wherein the plurality of individual magnetic segments has a total magnetic segment length that is greater than a total magnetic implant length of at least one of the first and second magnetic implants.

12. A positioning wand for assisting in positioning at least one of a first magnetic implant and a second magnetic implant configured for forming an anastomosis between two adjacent walls of a digestive tract of a patient, the positioning wand comprising:
an elongated member sized and configured to have at least a portion thereof to be inserted into an abdominal cavity of the patient, the elongated member comprising a plurality of tubular structures coupled to each other in a telescopic configuration to lengthen the elongated member to a deployable configuration and to shorten the elongated member to a retracted configuration; and
a distal tip provided at a distal end of the elongated member and comprising a guide magnet configured to magnetically couple with the at least one of the first and second magnetic implants through a wall of the digestive tract to translate the at least one of the first and second magnetic implants along an inner surface of the wall of the digestive tract to a desired site of the anastomosis, the distal tip being configured for placement against an outer surface of the wall of the digestive tract to be moveable in response to a contact pressure upon contact with the outer surface of the wall of the digestive tract.

13. The positioning wand of claim 12, wherein the plurality of tubular structures defines a channel extending along a longitudinal axis of the elongated member, the channel being configured to receive a guide wire therein.

14. The positioning wand of claim 13, wherein the elongated member comprises a flexible portion, and the guide wire is configured to steer the flexible portion to assist in deploying the distal tip to a given location in the digestive tract.

15. A positioning wand for assisting in positioning at least one of a first magnetic implant and a second magnetic implant configured for forming an anastomosis between two adjacent walls of a digestive tract of a patient, the positioning wand comprising:
- an elongated member sized and configured to have at least a portion thereof to be inserted into an abdominal cavity of the patient, the elongated member comprising:
  - a tubular structure defining a channel extending along a longitudinal axis of the elongated member, the channel being configured to receive a guide wire therein; and
- a distal tip provided at a distal end of the elongated member and comprising a guide magnet configured to magnetically couple with the at least one of the first and second magnetic implants through a wall of the digestive tract to translate the at least one of the first and second magnetic implants along an inner surface of the wall of the digestive tract to a desired site of the anastomosis, the distal tip being configured for placement against an outer surface of the wall of the digestive tract to be moveable in response to a contact pressure upon contact with the outer surface of the wall of the digestive tract;
  wherein the guide wire is connected to the distal tip to form a flexible connection between the distal end of the elongated member and the distal tip.

16. The positioning wand of claim 15, wherein the elongated member comprises a flexible portion, and the guide wire is configured to steer the flexible portion to assist in deploying the distal tip to a given location in the digestive tract.

17. The positioning wand of claim 15, wherein the distal tip is sized and configured to be received within the channel to alternate between a retracted configuration and a deployed configuration.

18. The positioning wand of claim 15, wherein the distal tip is connected to the guide wire.

19. The positioning wand of claim 15, wherein the distal tip is pivotally engaged with a distal end of the guide wire.

20. The positioning wand of claim 15, wherein the distal tip is connected to a longitudinally extending instrument provided within the channel of the elongated member.

21. The positioning wand of claim 20, wherein the distal tip is pivotally engaged with a distal end of the longitudinally extending instrument.

22. The positioning wand of claim 15, wherein the distal tip is releasable from the elongated member while remaining connected to the guide wire.

23. The positioning wand of claim 15, wherein the distal tip and the guide wire are releasable from the elongated member.

* * * * *